United States Patent
Hong et al.

(10) Patent No.: US 11,641,416 B2
(45) Date of Patent: *May 2, 2023

(54) DISPLAY DEVICE

(71) Applicant: SAMSUNG DISPLAY CO., LTD., Yongin-si (KR)

(72) Inventors: Won Ki Hong, Suwon-si (KR); So Hee Park, Cheonan-si (KR); Hee Seomoon, Hwaseong-si (KR); Hyeon Jun Lee, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,164

(22) Filed: Mar. 28, 2022

(65) Prior Publication Data

US 2022/0217227 A1 Jul. 7, 2022

Related U.S. Application Data

(63) Continuation of application No. 16/920,073, filed on Jul. 2, 2020, now Pat. No. 11,290,583.

(30) Foreign Application Priority Data

Sep. 3, 2019 (KR) .......................... 10-2019-0108654

(51) Int. Cl.
*H04M 1/02* (2006.01)
*H01L 27/32* (2006.01)

(52) U.S. Cl.
CPC ........ *H04M 1/0266* (2013.01); *H01L 27/323* (2013.01); *H04M 2250/12* (2013.01)

(58) Field of Classification Search
CPC . A61B 5/02108; A61B 5/0261; A61B 5/6826; A61B 5/6898; A61B 2562/0247;
(Continued)

(56) References Cited

U.S. PATENT DOCUMENTS 10,268,884 B2 4/2019 Jones et al.
10,813,561 B2 10/2020 Kwon et al.
(Continued)

FOREIGN PATENT DOCUMENTS

CN 105748053 A 7/2016
EP 2330819 A2 6/2011
(Continued)

OTHER PUBLICATIONS

EPO Extended Search Report dated Feb. 20, 2020, for corresponding European Patent Application No. 19200107.1 (10 pages).
(Continued)

*Primary Examiner* — Nelson M Rosario
(74) *Attorney, Agent, or Firm* — Lewis Roca Rothgerber Christie LLP

(57) ABSTRACT

A display device includes a display panel to display an image, and a blood pressure measuring module including a pressure sensor and a pulse wave sensor, wherein the pressure sensor is configured to sense a pressure that is applied to the display panel, the pulse wave sensor includes an optical sensor, and the pulse wave sensor is configured to generate a pulse wave signal using light that is emitted from a pixel of the display panel.

18 Claims, 39 Drawing Sheets

(58) Field of Classification Search
CPC .......... A61B 2562/046; A61B 5/02416; A61B 5/02007; A61B 5/02116; A61B 5/02125; A61B 5/022; A61B 5/02225; A61B 5/02427; A61B 5/1036; A61B 5/681; A61B 5/6824; A61B 5/6843; A61B 5/72; A61B 5/746; H01L 27/323; H04M 1/0266; H04M 2250/12; G06F 3/044; G06T 11/206
See application file for complete search history.

(56) References Cited

U.S. PATENT DOCUMENTS

| | | |
|---|---|---|
| 2002/0167531 A1 | 11/2002 | Baudisch |
| 2011/0215712 A1 | 9/2011 | Hong |
| 2013/0135328 A1 | 5/2013 | Rappoport et al. |
| 2013/0154910 A1 | 6/2013 | Chu et al. |
| 2013/0208017 A1 | 8/2013 | Gu et al. |
| 2015/0144891 A1 | 5/2015 | Park |
| 2016/0111487 A1 | 4/2016 | Jeong et al. |
| 2016/0302735 A1 | 10/2016 | Noguchi et al. |
| 2016/0310027 A1 | 10/2016 | Han |
| 2017/0162111 A1 | 6/2017 | Kang et al. |
| 2017/0178566 A1 | 6/2017 | Xu et al. |
| 2017/0251935 A1 | 9/2017 | Yuen |
| 2018/0005561 A1 | 1/2018 | Moon et al. |
| 2018/0040682 A1 | 2/2018 | Ebisuno et al. |
| 2018/0055388 A1 | 3/2018 | Morikawa et al. |
| 2018/0177413 A1 | 6/2018 | Kwon et al. |
| 2018/0228383 A1* | 8/2018 | Warisawa .............. A61B 5/352 |
| 2019/0008399 A1 | 1/2019 | Mukkamala et al. |
| 2019/0015000 A1 | 1/2019 | Han |
| 2019/0130822 A1 | 5/2019 | Jung et al. |
| 2021/0065620 A1 | 3/2021 | Yang et al. |
| 2021/0067618 A1 | 3/2021 | Hong et al. |

FOREIGN PATENT DOCUMENTS

| | | |
|---|---|---|
| EP | 3002790 A1 | 4/2016 |
| EP | 3 342 336 A1 | 7/2018 |
| KR | 10-1346980 B1 | 1/2014 |
| KR | 10-2014-0092119 A | 7/2014 |
| KR | 10-2017-0049280 A | 5/2017 |
| KR | 10-2017-0067077 A | 6/2017 |
| KR | 10-2017-0113066 A | 10/2017 |
| KR | 10-2017-0125778 A | 11/2017 |
| KR | 10-1813459 B1 | 1/2018 |
| KR | 10-2018-0076050 A | 7/2018 |
| KR | 10-2019-0040527 A | 4/2019 |
| WO | WO 2016/176218 A1 | 11/2016 |

OTHER PUBLICATIONS

U.S. Office Action dated Aug. 20, 2020, issued in U.S. Appl. No. 16/507,733 (9 pages).

U.S. Office Action dated Mar. 19, 2021, issued in U.S. Appl. No. 16/507,733 (10 pages).

* cited by examiner

FIG. 12
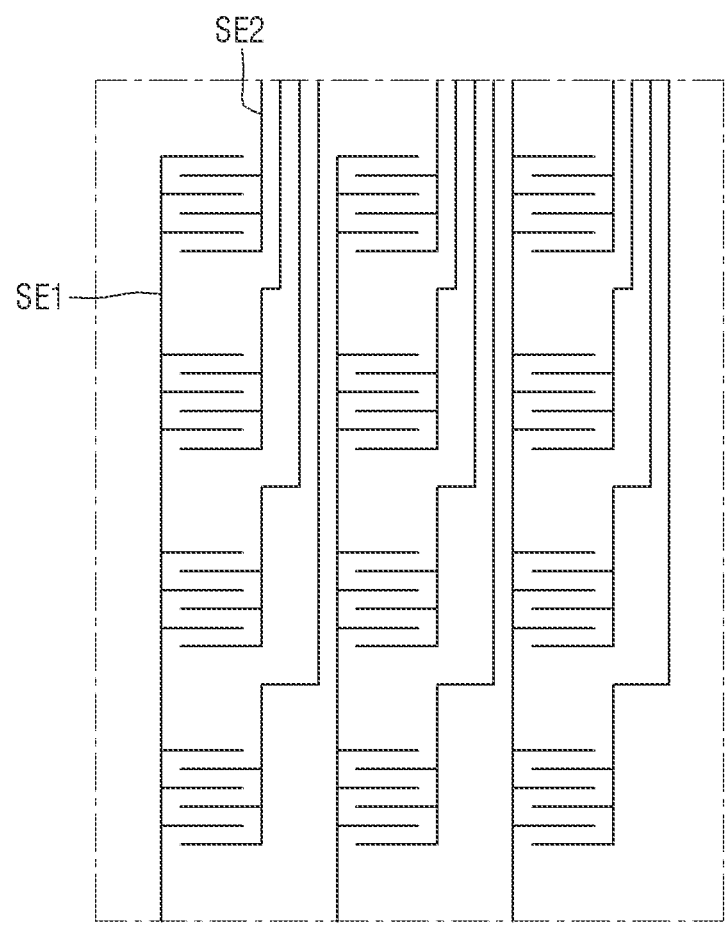
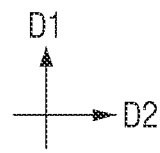

DISPLAY DEVICE

CROSS-REFERENCE TO RELATED APPLICATIONS

This application is a continuation of U.S. patent application Ser. No. 16/920,073, filed Jul. 2, 2020, which claims priority to and the benefit of Korean Patent Application No. 10-2019-0108654, filed Sep. 3, 2019, the entire content of both of which is incorporated herein by reference.

BACKGROUND

1. Field

The present disclosure relates to a display device, and more particularly, to a display device that has a blood pressure measuring function.

2. Description of Related Art

Display devices are devices that display an image and have been used not only for TVs and monitors, but also for portable smart phones, tablet personal computers (PCs), and the like. In the case of portable display devices, various functions are provided in the display devices. Examples thereof are cameras, fingerprint sensors, and the like.

Meanwhile, in recent years, as the healthcare industry has been in the spotlight, methods for more conveniently acquiring biometric information, which is related to health, have been developed. For example, such methods include attempting to change a traditional blood pressure measuring device using an oscillometric method into a portable electronic product. This is because the electronic blood pressure measuring device requires its own independent light source, sensor, and display, and it is inconvenient to carry the electronic blood pressure measuring device separately.

SUMMARY

One or more aspects of embodiments of the present disclosure are directed toward a display device in which a blood pressure measuring module is integrated.

It should be noted that objects of the present disclosure are not limited to the above-described objects, and other objects of the present disclosure will be apparent to those skilled in the art from the following descriptions.

According to an exemplary embodiment of the present disclosure, a display device includes a display panel to display an image; and a blood pressure measuring module including a pressure sensor and a pulse wave sensor, wherein the pressure sensor is configured to sense a pressure that is applied to the display panel, the pulse wave sensor includes an optical sensor, and the pulse wave sensor is configured to generate a pulse wave signal using light that is emitted from a pixel of the display panel.

In an exemplary embodiment, the pressure sensor and the optical sensor overlap the display panel in a thickness direction.

In an exemplary embodiment, the pressure sensor and the optical sensor overlap each other in the thickness direction.

In an exemplary embodiment, the optical sensor is below the display panel, and the pressure sensor is transparent and is between the display panel and the optical sensor.

In an exemplary embodiment, the optical sensor is below the display panel, and the pressure sensor is transparent and is above the display panel.

In an exemplary embodiment, the display device includes a display area and a non-display area, and the pressure sensor and the optical sensor are in the display area.

In an exemplary embodiment, the optical sensor is outside the display panel, and the pressure sensor overlaps the display panel in a thickness direction.

In an exemplary embodiment, the optical sensor overlaps the pressure sensor.

In an exemplary embodiment, the optical sensor does not overlap the pressure sensor and is positioned within a distance of about 30 mm from the pressure sensor in a horizontal direction.

In an exemplary embodiment, the blood pressure measuring module further includes a control part configured to measure a blood pressure using a pressure signal, which is sensed by the pressure sensor, and the pulse wave signal that is received from the pulse wave sensor.

In an exemplary embodiment, the blood pressure measuring module is configured to concurrently measure blood pressures at a plurality of points above the display panel.

In an exemplary embodiment, the display panel includes a plurality of pixel electrodes and a common electrode, the common electrode includes a light transmission opening, and the optical sensor overlaps the light transmission opening.

In an exemplary embodiment, the pressure sensor includes a force sensor, a gap capacitor, or a strain gauge.

In an exemplary embodiment, the display device further includes a window member that is above the display panel.

In an exemplary embodiment, the window member includes a glass having a thickness of about 0.2 mm or less or a transparent polymer having a thickness of about 0.1 mm or less.

According to an exemplary embodiment of the present application, a display device includes a display panel that includes a display area including a display light-transmission area and a display-only area, a pressure sensor that overlaps the display panel in a thickness direction, and an optical sensor that is disposed below the display panel and overlaps the display light-transmission area of the display panel, wherein the display light-transmission area includes a plurality of first pixels and a light transmission part, the display-only area includes a plurality of second pixels, the light transmission part has a light transmittance higher than that of each of the first pixels and each of the second pixels, and the display light-transmission area has a light transmittance higher than that of the display-only area.

In an exemplary embodiment, the pressure sensor overlaps the optical sensor in a thickness direction or is positioned within a distance of about 30 mm from the optical sensor in a horizontal direction.

In an exemplary embodiment, the pressure sensor is transparent and is between the optical sensor and the display panel.

In an exemplary embodiment, the optical sensor may use light that is emitted from the pixel of the display panel.

In an exemplary embodiment, the display panel includes a plurality of pixel electrodes and a common electrode, each of the pixel electrodes is over the display light-transmission area and the display-only area, the common electrode is on an entire surface in the display-only area, and the common electrode is in a region of the display light-transmission area and defines a light transmission opening.

BRIEF DESCRIPTION OF THE DRAWINGS

The above and other aspects and features of the present disclosure will become more apparent by describing exemplary embodiments thereof in detail with reference to the attached drawings, in which:

FIG. 12 is a schematic layout of a pressure sensor according to another exemplary embodiment;

DETAILED DESCRIPTION

Figure 1:
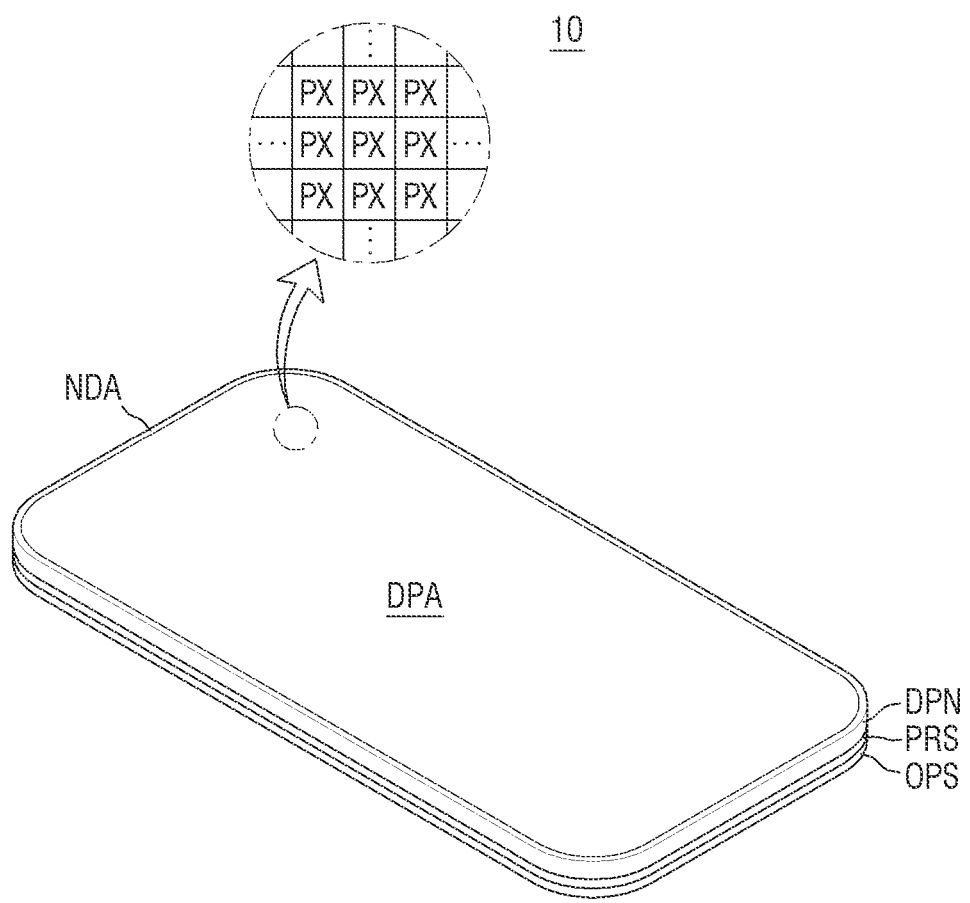
FIG. 1 is a schematic perspective view of a display device according to one exemplary embodiment.

The present invention will now be described more fully hereinafter with reference to the accompanying drawings, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

As used herein, the singular forms "a," "an," and "the" are intended to include the plural forms as well, unless the context clearly indicates otherwise.

It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, expressions such as "at least one of", "one of", and "selected from", when preceding a list of elements, modify the entire list of elements and do not modify the individual elements of the list.

As used herein, the term "and/or" includes any and all combinations of one or more of the associated listed items.

Further, the use of "may" when describing embodiments of the present disclosure refers to "one or more embodiments of the present disclosure".

As used herein, the phrases such as "a plan view" may refer to a view from top or from a direction normal to the display area (or display plane) of the display device.

Spatially relative terms, such as "below," "lower," "above," "upper," "bottom," "top" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" or "over" the other elements or features. Thus, the term "below" may encompass both an orientation of above and below. The device may be otherwise oriented (rotated 90 degrees or at other orientations), and the spatially relative descriptors used herein should be interpreted accordingly.

As used herein, the terms "substantially", "about", and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

As used herein, the terms "use," "using," and "used" may be considered synonymous with the terms "utilize," "utilizing," and "utilized," respectively.

It will also be understood that when a layer is referred to as being "on" another layer or substrate, it can be directly on the other layer or substrate, or intervening layers may also be present. In contrast, when an element is referred to as being "directly on" another element, there are no intervening elements present.

Like reference numerals in the figures denote like elements throughout, and redundant descriptions thereof may be omitted.

As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

FIG. 1 is a schematic perspective view of a display device according to one exemplary embodiment.

Referring to FIG. 1, a display device 10 displays a video or a still image. The display device 10 may include a display panel DPN. Examples of the display panel DPN include self-emissive display panels such as an organic light-emitting display (OLED) panel, an inorganic electro-luminescence (EL) display panel, a quantum dot light-emitting display (QLED) panel, a micro light-emitting display (micro LED) panel, a nano LED panel, a plasma display panel (PDP), a field emission display (FED) panel, and a cathode ray tube (CRT) display panel as well as light receiving display panels such as a liquid crystal display (LCD) panel and an electrophoretic display (EPD) panel. Hereinafter, the OLED panel will be described as an example of the display panel DPN, and the OLED panel applied to the exemplary embodiments will be simply referred to as the display panel DPN unless a special classification is required. However, the exemplary embodiments are not limited to the OLED panel, and other suitable display panels listed above or known in the art may be applied.

The display device 10 may further include a touch member. The touch member may be integrated with (e.g., may be a monolithic structure with) the display panel DPN or may be provided as a separate panel from the display panel DPN. The display device 10 may further include a sensor, various controllers, a housing, and/or other components in addition to the display panel DPN and the touch member. Any suitable device that includes a display area DPA configured to display an image or a video may be interpreted as corresponding to the display device 10 regardless of the primary use, any additional functionality, name, and/or other aspects of the device. Examples of the display device 10 may include, but are not limited to, a smartphone, a mobile phone, a tablet personal computer (PC), a personal digital assistant (PDA), a portable multimedia player (PMP), a television, a gaming machine, a wrist-watch type electronic device, a head-mounted display, a monitor of a PC, a notebook computer, a car navigation system, a car dashboard, a digital camera, a camcorder, an external advertisement board, an electric signboard, various medical devices, various inspection devices, various household appliances such as a refrigerator, a washing machine, and/or the like which includes a display part, an Internet of Things (IoT) device, and/or the like.

The display device 10 may include the display area DPA and a non-display area NDA. The display area DPA may be an active area that is an area in which an image is displayed, and the non-display area NDA may be an inactive area that is an area in which the image is not displayed. The display area DPA may have a rectangular planar shape, but the present disclosure is not limited thereto, and the display area DPA may have various planar shapes such as a square shape, a rhombus shape, a circular shape, and an elliptical shape. The non-display area NDA may be disposed around the display area DPA. The non-display area NDA may completely or partially surround the display area DPA. Signal lines through which signals are applied to the display area DPA or signals detected in the display area DPA are transmitted may be disposed in the non-display area NDA. The non-display area NDA, which is an inactive area, may correspond to a bezel area of the display device 10. Although the non-display area NDA is illustrated in the drawings (e.g., FIG. 1) as being disposed around all sides of the display area DPA that has a rectangular shape, the present disclosure is not limited thereto, and the non-display area NDA may not be disposed around some sides of the display area DPA or may be shown to be omitted in a plan view in such a manner that the non-display area NDA is bent to a rear surface of the display area DPA and overlaps the display area DPA in a thickness direction.

The display area DPA includes a plurality of pixels PX. The pixels PX are arranged in a matrix form. Each of the pixels PX may include an emission area (e.g., see "EMA" of FIG. 39). The emission area is, for example, an area in which an organic light-emitting layer is disposed to actually emit light, and a planar size of the emission area may be smaller than a planar size of each of the pixels PX (e.g., see "PX" and "EMA" of FIG. 39). An area in which a light-emitting material (i.e., an organic light-emitting layer) is not disposed in each of the pixels PX may be defined as a non-emission area (e.g., see "NEA" of FIG. 39). Circuits configured to drive the pixels PX or lines may be disposed in the non-emission area, but the present disclosure is not limited thereto.

The pixels PX may include a first color pixel, a second color pixel, and a third color pixel. The first color pixel may be a red pixel, the second color pixel may be a green pixel, and the third color pixel may be a blue pixel. In one exemplary embodiment, the arrangement of the pixels PX may be a stripe arrangement in which the pixels of the same color are arranged along a first direction D1 (a column extension direction) and the red pixel, the green pixel, and the blue pixel are alternately arranged along a second direction D2 (a row extension direction), in the order of the red pixel, the green pixel, and the blue pixel, but the arrangement of the pixels PX is not limited to the illustrated example. In one exemplary embodiment, the arrangement of the pixels PX may be a PENTILE® (PENTILE® is a registered trademark of Samsung Display Co., Ltd., Republic of Korea) arrangement in which each of the pixels PX is formed in a rhombus shape, and the red pixel and the blue pixel are arranged radially around the green pixel. In one exemplary embodiment, the pixels PX may further include a white pixel in addition to the red, green, and blue pixels.

In one exemplary embodiment, the display area DPA and/or the non-display area NDA may include a light transmission part that provides a light sensing-path. Descriptions of the light transmission part will be given in more detail below.

The display device 10 may further include a pressure sensor PRS. The pressure sensor PRS may at least partially overlap the display area DPA (e.g., in the thickness direction). That is, the pressure sensor PRS may be at least partially disposed in the display area DPA.

As an example, the entire pressure sensor PRS may overlap the display area DPA. As another example, a portion of the pressure sensor PRS may overlap the display area DPA and another portion may overlap the non-display area NDA. In one exemplary embodiment, the pressure sensor PRS may be disposed throughout the display area DPA of the display device 10 so that the entire display area DPA may overlap the pressure sensor PRS. In another exemplary embodiment, the pressure sensor PRS may be disposed only in a portion of the display device 10 so that a portion of the display area DPA may not overlap the pressure sensor PRS.

The display device 10 may include a blood pressure measuring module that uses an optical sensor OPS and the above-described pressure sensor PRS.

Figure 2:
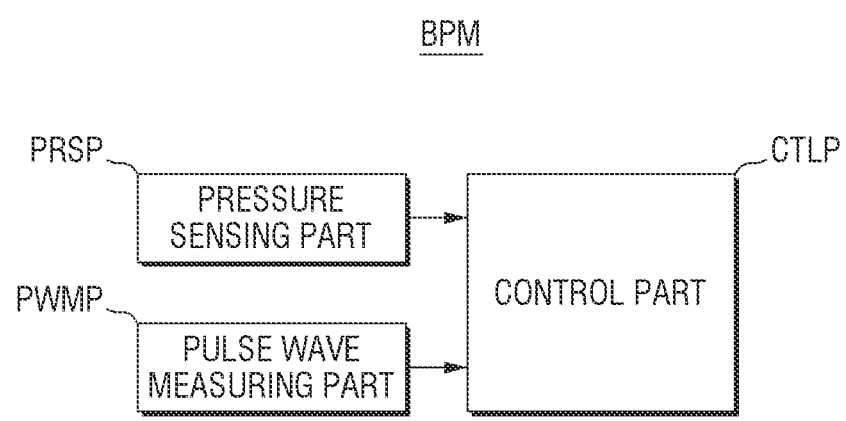
FIG. 2 is a schematic view of a blood pressure measuring module that is included in the display device according to one exemplary embodiment.

Reference is made to FIG. 2 for a more detailed description of the blood pressure measuring module.

FIG. 2 is a schematic view of the blood pressure measuring module that is included in the display device 10 according to one exemplary embodiment.

Referring to FIG. 2, a blood pressure measuring module BPM includes a pulse wave measuring part PWMP, a pressure sensing part PRSP, and a control part CTLP.

The pressure sensing part PRSP measures pressure that is applied by an object OBJ. The object OBJ is a part of a human body and may include, but is not limited to, a finger, a palm, a wrist, a toe, or the like. In order to measure a blood pressure, the display device 10 may need to be gradually pressurized (e.g., gradually increasing pressure) or gradually depressurized (e.g., gradually decreasing pressure), and/or maintained at a constant pressure by the object OBJ, and here, the pressure sensing part PRSP may determine whether the pressure is applied, and measure the magnitude of pressure, a change rate in pressure, and/or the like. Pressure signals, which are measured by the pressure sensing part PRSP, may be used to determine the effective time for measuring a pulse wave and to distinguish between a systolic blood pressure and a diastolic blood pressure.

The pressure sensing part PRSP may include the pressure sensor PRS. Examples of applicable pressure sensors PRS may include force sensors, strain gauges, gap capacitors, and the like. Descriptions thereof will be given in more detail below.

The pulse wave measuring part PWMP may include a pulse wave sensor. The pulse wave sensor may include a light source and an optical sensor that serves as a light-receiving element. Examples of the pulse wave sensor are illustrated in FIGS. 3-6.

FIGS. 3-6 are schematic views of the pulse wave sensors according to one or more exemplary embodiments.

Referring to FIGS. 3-6, the pulse wave sensor may include an optical sensor OPS (or a light-receiving element) that receives light reflected or scattered from the object OBJ. The optical sensor OPS may include, for example, a photodiode, a phototransistor, a complementary metal-oxide semiconductor (CMOS) or charge-coupled-device (CCD) image sensor, and/or the like. In one exemplary embodiment, a camera of the display device 10 may be applied (or used) as the optical sensor OPS, but the present disclosure is not limited thereto, and an optical sensor OPS separate from the camera may be disposed to receive light that is reflected or scattered from the object OBJ.

The pulse wave sensor may further include a light source. The light source may provide an inspection light. The wavelength of the inspection light may be an infrared wavelength, a visible light wavelength, a visible red wavelength, a visible green wavelength, a visible blue wavelength, or the like. The light source may include at least one of, for example, a light-emitting diode (LED), an organic light-emitting diode (OLED), a laser diode (LD), a quantum dot (QD), a phosphor, and a natural light.

Figure 3:
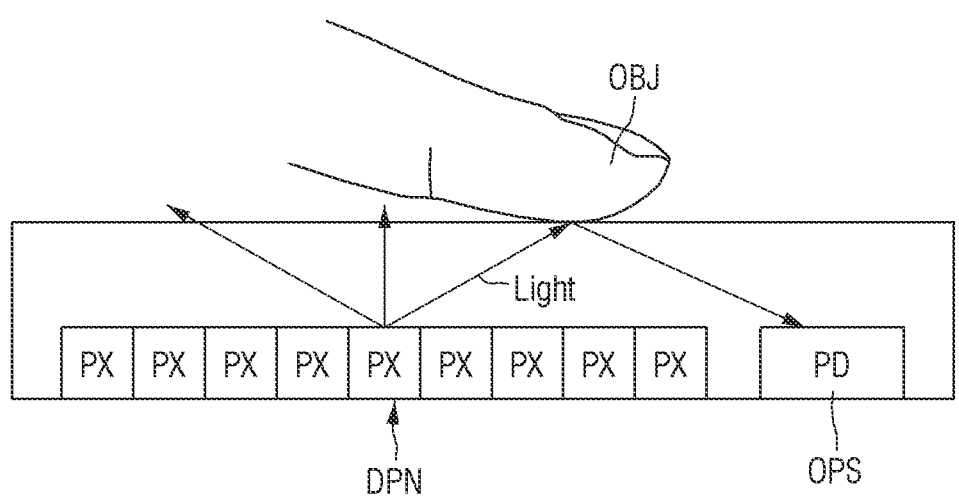
FIGS. 3-6 are schematic views of pulse wave sensors according to one or more exemplary embodiments.

As shown in FIG. 3, light emitted from the pixel PX of the display area DPA may be used as the inspection light, and in this case, the light source of the pulse wave sensor may include the pixel PX of the display panel DPN and/or a light-emitting layer included in the pixel PX. In the case of the exemplary embodiment of FIG. 3, a structure of the display device 10 may be simplified by using the light-emitting layer of the display panel DPN as the light source without providing a separate light source.

Figure 4:
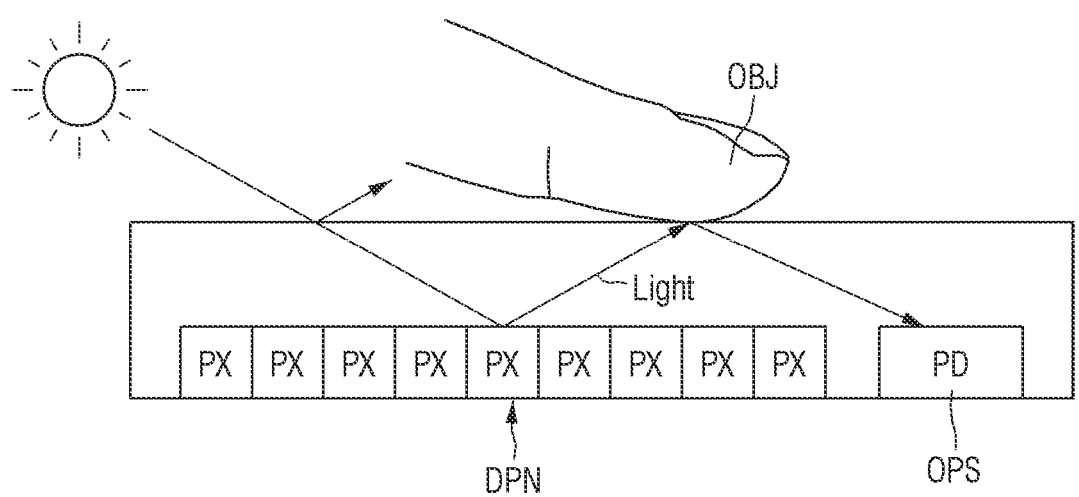

In another exemplary embodiment, external light may be used as the inspection light as illustrated in FIG. 4. In this case, the light source of the pulse wave sensor may include natural light and/or light in a region in which the display device 10 is positioned.

Figure 5:
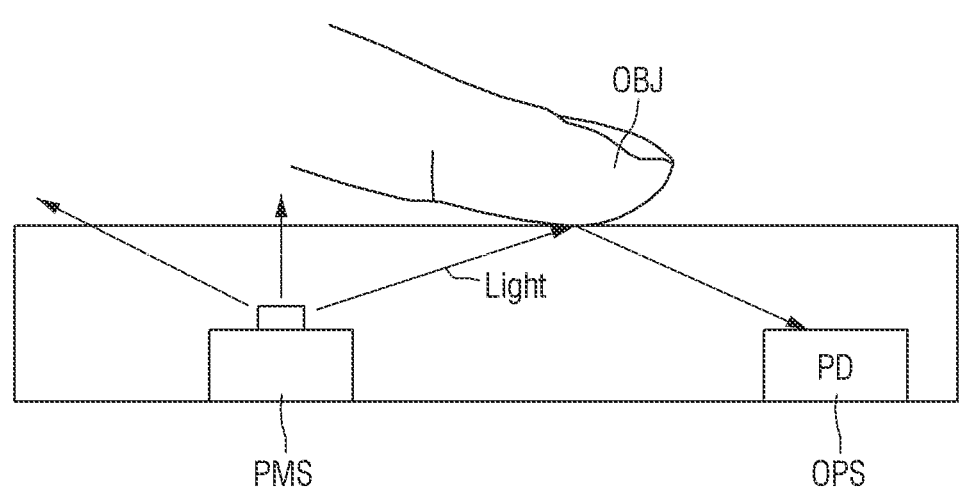

In still another exemplary embodiment, as shown in FIG. 5, the light source, which provides the inspection light, may be shared with a light source included in a proximity sensor PMS or another suitable sensor that is included in the display device 10.

Figure 6:
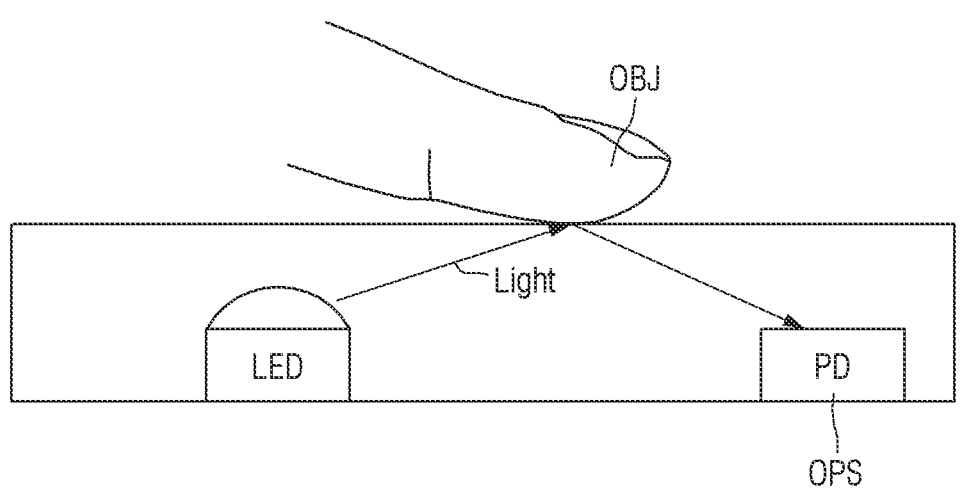

In yet another exemplary embodiment, as illustrated in FIG. 6, the pulse wave sensor of the display device 10 may further include an LED light source (LED) or an LD light source that is dedicated for pulse wave measurement.

Referring to FIG. 2, the pulse wave measuring part PWMP measures a photoplethysmography (PPG) signal (hereinafter, referred to as a "pulse wave signal") from the object OBJ using a light source and a pulse wave sensor. The PPG signal has a waveform that reflects a change in the volume of a blood vessel at a peripheral part according to the heart beating. Blood, which is ejected from a left ventricle of a heart in (or during) a systolic phase of the heart (i.e., the phase of the heartbeat when the heart muscle contracts and pumps blood from the chambers into the arteries), is moved to peripheral tissues, causing an increase in blood volume at an artery side. In addition, in the systolic phase of the heart, red blood cells carry more oxygen hemoglobin to the peripheral tissues. In (or during) a diastolic phase of the heart (i.e., the phase of the heartbeat when the heart muscle relaxes and allows the chambers to fill with blood), the blood is partially suctioned into or fills the heart from the peripheral tissues. When light is irradiated to peripheral blood vessels, the irradiated light is absorbed by the peripheral tissues. Here, light absorbance is dependent on hematocrit (i.e., the ratio of the volume of red blood cells to the total volume of blood) and blood volume. The light absorbance may have the maximum value at the systolic phase of the heart and the minimum value at the diastolic phase of the heart. The pulse wave signal reflects the maximum value of the light absorbance at the systolic phase of the heart and the minimum value of the light absorbance at the diastolic phase of the heart. In addition, the pulse wave signal shows a phenomenon which vibrates or fluctuates according to a heartbeat cycle. Accordingly, the pulse wave signal may reflect the change in blood pressure according to the heartbeat and thus may be used for a blood pressure measurement.

The control part CTLP may be configured by a device capable of computing, such as a microprocessor. In one or more exemplary embodiments, the control part CTLP includes a device capable of computing, such as a microprocessor. The control part CTLP may measure a blood pressure using the pressure signal, which is sensed by the pressure sensing part PRSP, and the pulse wave signal that is received by the pulse wave measuring part PWMP.

For example, in a process in which a user touches the display device 10 with his or her finger and then removes the finger from the display device 10, there is a change in a pressure (contact pressure) applied to the pressure sensor PRS (i.e., the pressure gradually increases to reach the maximum value and then gradually decreases). When the contact pressure increases, a blood vessel may shrink, causing blood flow to decrease or become zero. When the contact pressure decreases, the blood vessel may expand, causing blood flow to increase or become greater than zero (i.e., causing the blood to flow again). When the contact pressure further decreases, the blood flow becomes greater. Because the amount of light absorbed by the pulse wave sensor is proportional to the change in blood flow and the transmitted light detected (or received) by the pulse wave sensor is subtracted by the amount of light absorbed by the finger, the change in the amount of light of the transmitted light reflects the change in blood flow. Accordingly, the pulse wave sensor may detect the change in blood volume, which is synchronized with the heartbeat, by measuring the amount of light, and thus, the control part CTLP may estimate blood pressures of a part of the object based on time differences between a time point corresponding to a peak of the detected pulse wave signal and a time point corresponding to a peak of a filtered pulse wave. Among the estimated blood pressures, the blood pressure having the maximum magnitude may be estimated as a systolic blood pressure and the blood pressure having the minimum magnitude may be estimated as a diastolic blood pressure. Further, other type (e.g., other types of data) of blood pressures, such as an average blood pressure, may be estimated or calculated using the estimated, measured, or determined blood pressures.

Figure 7:
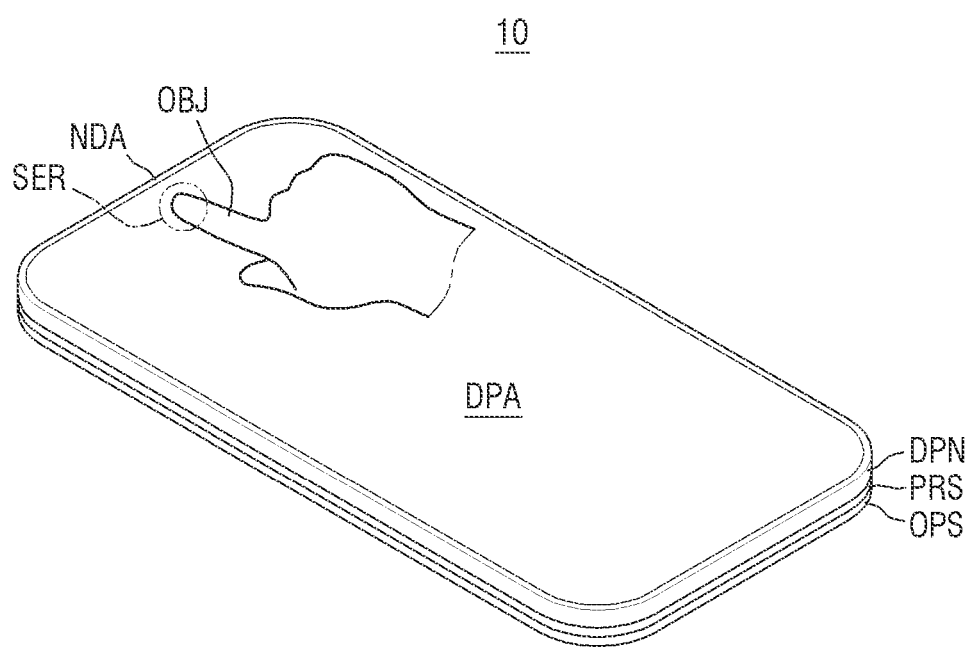
FIG. 7 is a schematic perspective view illustrating a state of measuring a blood pressure in the display device according to one exemplary embodiment.
Figure 8:
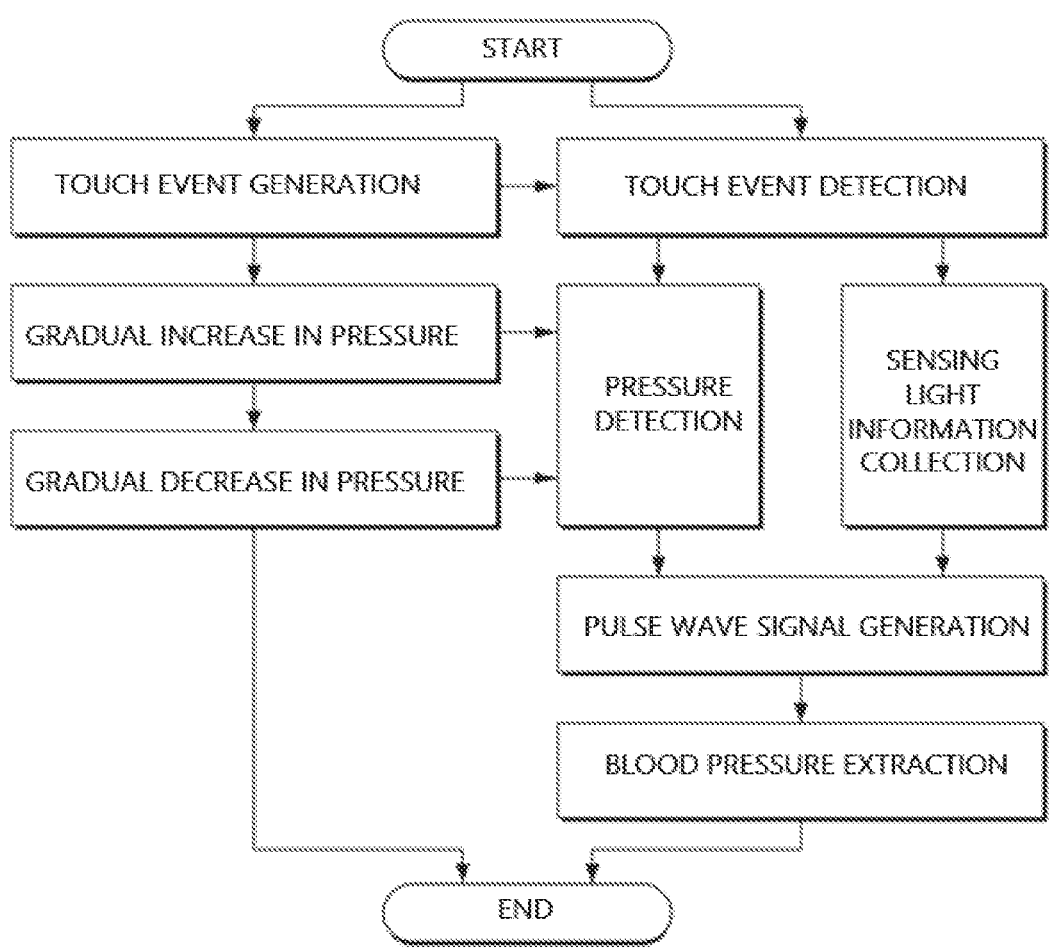
FIG. 8 is a flowchart illustrating a method of measuring the blood pressure in the display device according to one exemplary embodiment.

FIG. 7 is a schematic perspective view illustrating a state of measuring a blood pressure in the display device according to one exemplary embodiment. FIG. 8 is a flowchart illustrating a method of measuring the blood pressure in the display device according to one exemplary embodiment.

Referring to FIGS. 7 and 8, when a touch event occurs, the display device 10 recognizes the touch event. The touch event may occur while a subject touches one point SER of the display device 10 with a part (e.g., the object OBJ illustrated in FIG. 7) of his or her body. Recognition of the touch event may be performed by the touch member and/or the pressure sensor PRS of the display device 10.

The touch event may be applied commonly in (or occur during) a touch mode or a blood pressure measurement mode. Accordingly, the display device 10 may be set in advance whether to drive the touch event in the touch mode or in the blood pressure measurement mode. For example, a user who wants to measure his or her blood pressure may pre-determine that the subsequently occurring touch event is for a blood pressure measurement by setting the operation mode as the blood pressure measurement mode through a program or application of the display device 10 before the user inputs a touch (e.g., touches the display device 10 with an object OBJ).

In one or more exemplary embodiments, the display device 10 may automatically switch to the blood pressure measurement mode by grasping the location and pressure of the touch event without a separate mode determination operation of the user (e.g., without input from the user). For example, when a location where the touch event occurs is a location irrelevant to a blood pressure measurement location (e.g., a location of the display device 10 that is not capable of functioning as a blood pressure measurement location or is not intended to measure blood pressure), the display device 10 may operate in the touch mode, and when the location where the touch event occurs is a location that is irrelevant to a touch input (e.g., a location of the display device 10 that is intended to function only as a blood pressure measurement location) and corresponds to the blood pressure measurement location, the display device 10 may operate in the blood pressure measurement mode. In addition, when the location where the touch event occurs is a location that corresponds to both the touch input and the blood pressure measurement location (e.g., the touch input and the blood pressure measurement location is the same location), the display device 10 may operate by automatically switching to the blood pressure measurement mode through a pressing force analysis (e.g., measuring an attribute of the applied pressure such as duration and/or force applied by the pressing force) of the pressure sensor PRS, which is received after waiting for the operation mode to be selected (e.g., an operation mode has not been selected by the user). In one or more exemplary embodiments, the display device 10 may switch to the blood pressure measurement mode after the pressing force has been applied for a set duration of time and/or a certain amount of force is applied, but the present disclosure is not limited thereto. For example, one of ordinary skill in the art would appreciate that any suitable triggering mechanism based on any attribute of the pressing force or duration may be used.

Next, when the user gradually increases and then gradually decreases the contact pressure, during the corresponding process, the pressure sensor PRS measures the change in pressure, while optical information, which is sensed through the light reflected or scattered by the object OBJ, is collected by the pulse wave sensor.

Subsequently, the control part CTLP generates a pulse wave signal according to the change in pressure, which is obtained from the pressure sensor PRS, and the sensed light information that is obtained from the pulse wave sensor and extracts the blood pressure based on the pulse wave signal. The measured blood pressure may be displayed through the display area DPA of the display device 10.

The above-described blood pressure measuring module BPM and the method of measuring the blood pressure are only exemplary, and other various methods are disclosed in Korean Patent Publication No. 10-2018-0076050 published on Jul. 5, 2018, Korean Patent Publication No. 10-2017-0049280 published on May 10, 2017, Korean Patent Publication No. 10-2019-0040527 published on Apr. 19, 2019, and the like, and the entire contents disclosed in each of the above patent publications are incorporated by reference and integrated herein as if fully disclosed in the present specification.

Figure 9:
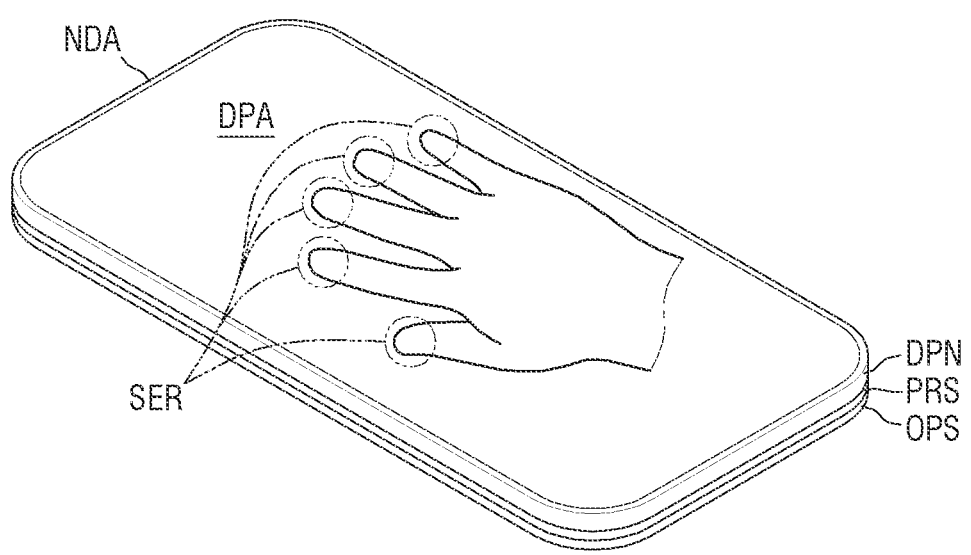
FIG. 9 is a schematic perspective view illustrating a state of measuring a blood pressure in a display device according to another exemplary embodiment.

FIG. 9 is a schematic perspective view illustrating a state of measuring blood pressure in the display device according to another exemplary embodiment. The exemplary embodiment of FIG. 9 illustrates that the display device 10 may concurrently (e.g., simultaneously) perform a plurality of blood pressure measurements.

Referring to FIG. 9, the display device 10 may measure blood pressures at two or more points SER. That is, the display device 10 may perform multiple blood pressure measurements. In one exemplary embodiment, the pressure sensor PRS and the optical sensor OPS may be separately provided at each of the plurality of points SER. In another exemplary embodiment, a blood pressure may be measured by making one pressure sensor PRS and one optical sensor OPS cover a wide region, and the blood pressure may be measured by sensing pressure and pulse wave signals at the plurality of points SER within the corresponding region. In this case, points in which a plurality of touch events are generated may be configured by the touch member and/or the pressure sensor PRS. In one or more exemplary embodiments, the one pressure sensor PRS and the one optical sensor OPS covering a wide region may distinguish between the plurality of points SER within the corresponding region to perform multiple blood pressure measurements concurrently (e.g., simultaneously).

The multiple blood pressure measurements may be performed, for example, for different fingers of the same user. For example, a finger of a right hand and a finger of a left hand as the objects OBJ may concurrently (e.g., simultaneously) touch the touch member and/or the pressure sensor PRS of the display device (e.g., at two or more points SER), and each pulse wave signal for the corresponding finger may be measured. In addition, pulse wave signals for a plurality of fingers of one hand may also be measured. For example, as illustrated in FIG. 9, all of the fingers of one hand may touch the touch member and/or the pressure sensor PRS of the display device, and a pulse wave signal may be measured from each finger that touches the touch member and/or the pressure sensor PRS of the display device. As described above, when a plurality of blood pressure measurement results are obtained from the same user, the results may be averaged or the blood pressure for each part may be divided to estimate and output the average systolic and/or diastolic blood pressure.

The multiple blood pressure measurements may be utilized to concurrently (e.g., simultaneously) measure blood pressures of fingers of a plurality of users. In this case, the blood pressure measured for each user may be distinguished and output.

Hereinafter, structures of the pressure sensors PRS according to one or more exemplary embodiments will be described in more detail.

Figure 10:
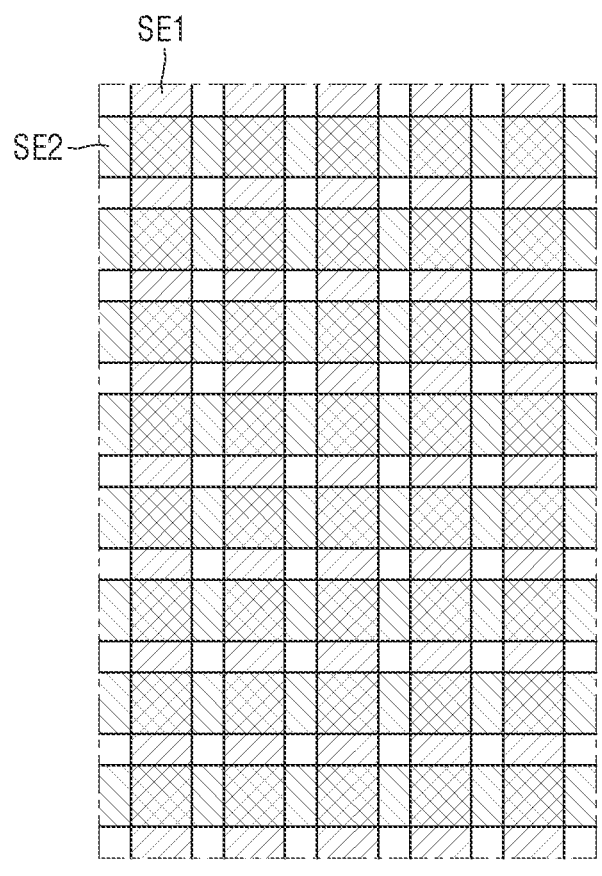
FIG. 10 is a schematic layout of a pressure sensor according to one exemplary embodiment.
Figure 11:
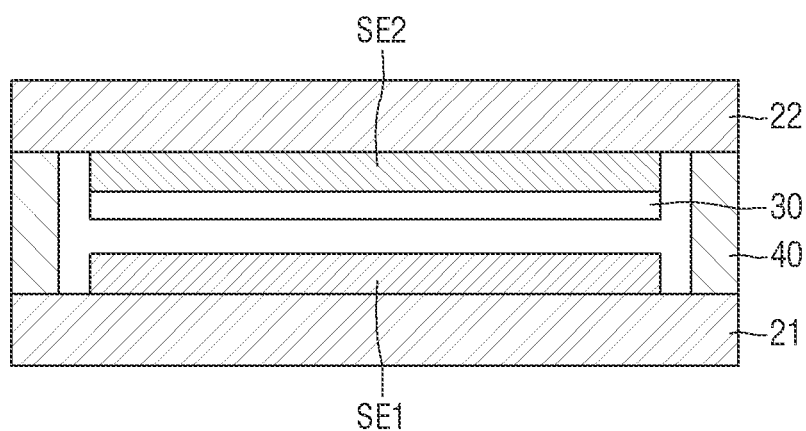
FIG. 11 is a cross-sectional view of the pressure sensor of FIG. 10.

FIG. 10 is a schematic layout of a pressure sensor according to one exemplary embodiment. FIG. 11 is a cross-sectional view of the pressure sensor of FIG. 10. FIGS. 10 and 11 exemplarily illustrate the structure of a force sensor that is an example of the pressure sensor according to one or more exemplary embodiments.

Referring to FIGS. 10 and 11, the pressure sensor may include a first electrode SE1, a second electrode SE2, and a pressure-sensing layer 30 that is disposed between the first electrode SE1 and the second electrode SE2.

Each of the first electrode SE1 and the second electrode SE2 may be made of a conductive material. For example, each of the first electrode SE1 and the second electrode SE2 may be made of a metal such as silver (Ag) or copper (Cu), a transparent conductive oxide such as indium tin oxide (ITO), indium zinc oxide (IZO), or indium zinc tin oxide (IZTO), a carbon nanotube, a conductive polymer, and/or the like. One of the first electrode SE1 and the second electrode SE2 may be a driving electrode, and the other one may be a sensing electrode.

The pressure-sensing layer 30 may include a pressure-sensitive material. The pressure-sensitive material may include metal nanoparticles such as nickel, aluminum, tin, and copper, and/or carbon. The pressure-sensitive material may be disposed in a polymer resin in the form of a particle, but the present disclosure is not limited thereto. The pressure-sensitive material of the pressure-sensing layer 30 has a low electrical resistance as pressure applied thereto increases, and thus it is possible to sense whether the pressure is applied and sense the magnitude of the pressure by measuring an electrical resistance of the pressure-sensing layer 30 through the first electrode SE1 and the second electrode SE2. The pressure-sensing layer 30 may be formed to be transparent or opaque.

In one or more exemplary embodiments, a plurality of first electrodes SE1 may be arranged in a line type and a plurality of second electrodes SE2 may be arranged in a line type. For example, the plurality of first electrodes SE1 may extend in the first direction D1 while being parallel to each other, and the plurality of second electrodes SE2 may extend in the second direction D2 that intersects the first direction D1. In one or more exemplary embodiments, the second direction D2 is perpendicular to or normal to the first direction D1. The plurality of first electrodes SE1 and the plurality of second electrodes SE2 have a plurality of overlapping regions at portions where the plurality of first electrodes SE1 and the plurality of second electrodes SE2 overlap (or cross) each other (e.g., as illustrated in the embodiment of FIGS. 10 and 11). The overlapping regions may have a matrix arrangement (e.g., as illustrated in the embodiment of FIG. 10). Each of the overlapping regions may become a pressure sensing cell. That is, the pressure-sensing layer 30 may be disposed in each of the overlapping regions such that pressure sensing may be performed at a corresponding position.

In one exemplary embodiment, the pressure sensor may include two sensor substrates that are facing each other. Each of the sensor substrates may include a substrate 21 or 22. Each of a first substrate 21 of a first sensor substrate and a second substrate 22 of a second sensor substrate may include a polyethylene-based, polyimide-based, polycarbonate-based, polysulfone-based, polyacrylate-based, polystyrene-based, polyvinyl chloride-based, polyvinyl alcohol-based, polynorbornene-based, and/or polyester-based material. In one exemplary embodiment, the first substrate 21 and the second substrate 22 may be composed of a polyethylene terephthalate (PET) film or a polyimide film.

The first electrode SE1, the second electrode SE2, and the pressure-sensing layer 30 may be included in the first sensor substrate or the second sensor substrate. For example, the first electrode SE1 and the pressure-sensing layer 30 may be included in the first sensor substrate, and the second electrode SE2 may be included in the second sensor substrate. The first electrode SE1 may be disposed on or at one surface of the first substrate 21, which faces the second substrate 22. The second electrode SE2 may be disposed on or at one surface of the second substrate 22, which faces the first substrate 21. In one or more exemplary embodiments, the first electrode SE1 and the second electrode SE2 are disposed at different layers (e.g., the first electrode SE1 is disposed at a layer below the second electrode SE2). In one or more exemplary embodiments, the pressure-sensing layer 30 may be disposed on the second electrode SE2. The first sensor substrate and the second sensor substrate may be coupled to each other using a coupling layer 40. The coupling layer 40 may be disposed along an edge of each sensor substrate, but the present disclosure is not limited thereto. In one or more exemplary embodiments, the coupling layer 40 is spaced apart from the pressure-sensing layer 30, the first electrode SE1, and/or the second electrode SE2 as illustrated in FIG. 11.

In another exemplary embodiment, a first electrode SE1, a second electrode SE2, and a pressure-sensing layer 30 may be included in one sensor substrate. For example, the first electrode SE1 may be disposed on one surface of a first substrate 21, the pressure-sensing layer 30 may be disposed on the first electrode SE1, and the second electrode SE2 may be disposed on the pressure-sensing layer 30.

The pressure sensor including the above-described force sensor may be formed to be transparent or opaque. In the case of the transparent pressure sensor, it is apparent that the first substrate 21 and the second substrate 22 are made of a transparent material, and also, the first electrode SE1 and the second electrode SE2 may be made of a transparent conductive material, and the pressure-sensing layer 30 may be made of a transparent material. In the case of the opaque pressure sensor, an electrode or pressure-sensitive material may be selected from a variety of materials regardless of transparency (i.e., materials may be opaque, transparent, or have a degree of transparency therebetween).

Figure 13:
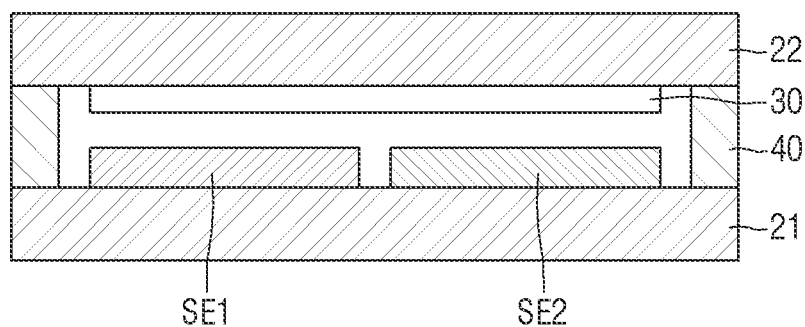
FIG. 13 is a cross-sectional view of the pressure sensor of FIG. 12.

FIG. 12 is a schematic layout of a pressure sensor according to another exemplary embodiment. FIG. 13 is a cross-sectional view of the pressure sensor of FIG. 12. FIGS. 12 and 13 exemplarily illustrate another structure of a force sensor according to one or more exemplary embodiments.

Referring to FIGS. 12 and 13, the pressure sensor according to the illustrated exemplary embodiment is different from that of the exemplary embodiment described with reference to FIGS. 10 and 11 in that a first electrode SE1 and a second electrode SE2 are disposed on the same layer. Specifically, for example, the first electrode SE1 and the second electrode SE2 are disposed on one surface of a first substrate 21. The first electrode SE1 and the second electrode SE2 are disposed to be adjacent to each other. The first electrode SE1 and the second electrode SE2 may each include a plurality of branch portions and may have the form of a comb electrode in which the branch portions are alternately arranged. A pressure-sensing layer 30 is formed on a second substrate 22 and disposed above the first electrode SE1 and the second electrode SE2.

In the case of the illustrated exemplary embodiment, the first electrode SE1 and the second electrode SE2 do not overlap each other in a thickness direction but are disposed to be adjacent to each other (e.g., as illustrated in the embodiment of FIG. 13 in a plan view). When pressure is applied, current may flow between the first electrode SE1 and the second electrode SE2, which are adjacent to each other, through the pressure-sensing layer 30 above the first electrode SE1 and the second electrode SE2. The above-described structure may be advantageous for measuring a shear stress.

Figure 14:
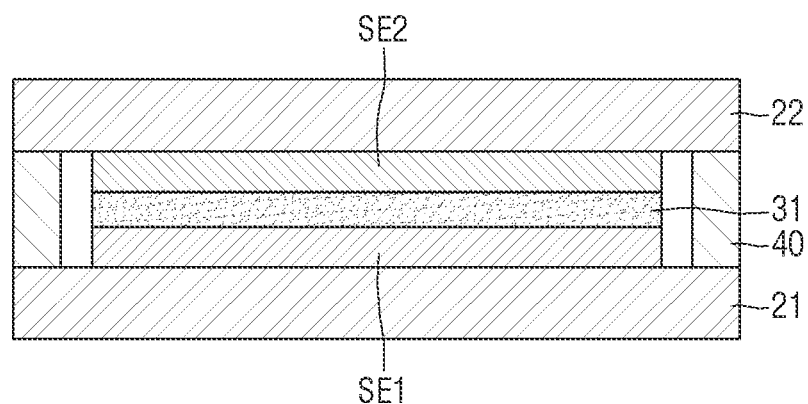
FIG. 14 is a cross-sectional view of a pressure sensor according to still another exemplary embodiment.

FIG. 14 is a cross-sectional view of a pressure sensor according to still another exemplary embodiment. FIG. 14 exemplarily illustrates a gap capacitor as an example of the pressure sensor.

Referring to FIG. 14, the pressure sensor according to the illustrated exemplary embodiment may include a first electrode SE1, a second electrode SE2, and a dielectric constant modifying material layer 31 that is disposed between the first electrode SE1 and the second electrode SE2. A pressure sensor PRS according to the illustrated exemplary embodiment may have a structure substantially the similar to the pressure sensor according to the exemplary embodiment described with reference to FIGS. 10 and 11 except that the dielectric constant modifying material layer 31 is disposed between the first electrode SE1 and the second electrode SE2 instead of the pressure-sensing layer 30.

The dielectric constant modifying material layer 31 is a material whose dielectric constant changes according to applied pressure, and various materials known in the art may be applied. Because the dielectric constant of the dielectric constant modifying material layer 31 varies according to the applied pressure, the magnitude of the applied pressure may be measured by measuring the value of a capacitance between the first electrode SE1 and the second electrode SE2.

The pressure sensor including the above-described gap capacitor may be formed to be transparent or opaque. In the case of the transparent pressure sensor, the first electrode SE1 and the second electrode SE2 may be made of a transparent conductive material, and the dielectric constant modifying material layer 31 may also be made of a transparent material. In the case of the opaque pressure sensor, an electrode or pressure-sensitive material may be selected from a variety of materials regardless of transparency (i.e., materials may be opaque, transparent, or have a degree of transparency therebetween).

Figure 15:
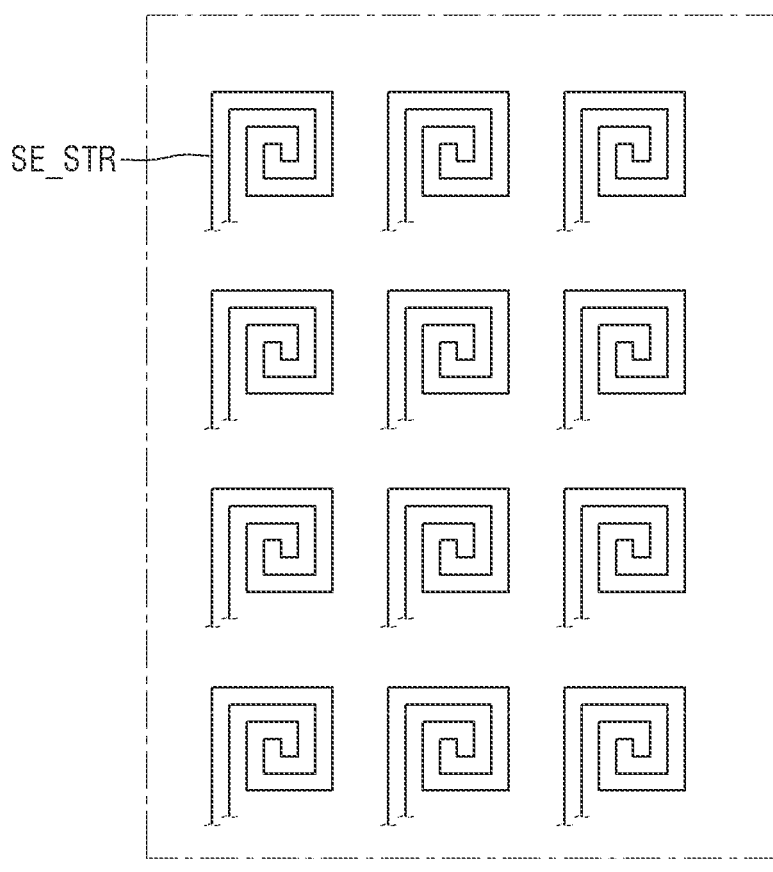
FIG. 15 is a schematic layout of the pressure sensor according to still another exemplary embodiment.

FIG. 15 is a schematic layout of the pressure sensor according to still another exemplary embodiment. FIG. 15 illustrates a strain gauge as an example of the pressure sensor.

Referring to FIG. 15, the pressure sensor PRS may include a strain sensing electrode SE_STR. The strain sensing electrode SE_STR may be formed of a pattern of a conductive layer that is formed on the first substrate (e.g., see "21" of FIG. 11). An insulating film or the second substrate (e.g., refer to "22" in FIG. 11) may be disposed on the strain sensing electrode SE_STR, but the present disclosure is not limited thereto.

The shape of the strain sensing electrode SE_STR changes as pressure is applied thereto. When the shape of the strain sensing electrode SE_STR changes, a resistance value thereof also changes. Accordingly, the magnitude of the pressure may be measured by measuring the value of the resistance across the strain sensing electrode SE_STR.

In order to maximize or increase the change in the resistance value according to the pressure, the strain sensing electrode SE_STR may have a winding shape, which includes a plurality of bent portions, in a plan view. For example, as illustrated in FIG. 15, the strain sensing electrode SE_STR may have a tornado shape in which the strain sensing electrode SE_STR extends to one side of the first direction D1 and is bent to extend to the other side of the second direction D2 and is then bent again to extend to the other side of the first direction D1 and bent again to extend to one side of the second direction D2, and this process is repeated. In one or more exemplary embodiments, the strain sensing electrode SE_STR includes a continuous electrode including a plurality of straight portions attached to each other by one or more corner portions where each of the plurality of straight portions is parallel or substantially parallel to another one of the plurality of straight portions. In one or more exemplary embodiments, each of the plurality of straight portions extends or extends substantially in either the first direction D1 or the second direction D2 where the first direction D1 is perpendicular to or normal to the second direction D2. As another example, the strain sensing electrode SE_STR may have a zigzag shape. However, it is to be understood that the planar shape of the strain sensing electrode SE_STR is not limited to that illustrated in the drawing, and suitable modifications may be made in various ways appreciated by one of ordinary skill in the art.

The pressure sensor including the above-described strain gauge may be formed to be transparent, opaque, or have a degree of transparency therebetween. In the case of the transparent pressure sensor, the strain sensing electrode SE_STR may be made of a transparent conductive material, and in the case of the opaque pressure sensor, the material of the strain sensing electrode SE_STR may be selected from various materials regardless of transparency (i.e., materials may be opaque, transparent, or have a degree of transparency therebetween).

Hereinafter, various arrangement relationships between the display panel DPN and the sensors PRS and OPS in the display device will be described in more detail.

Figure 16:
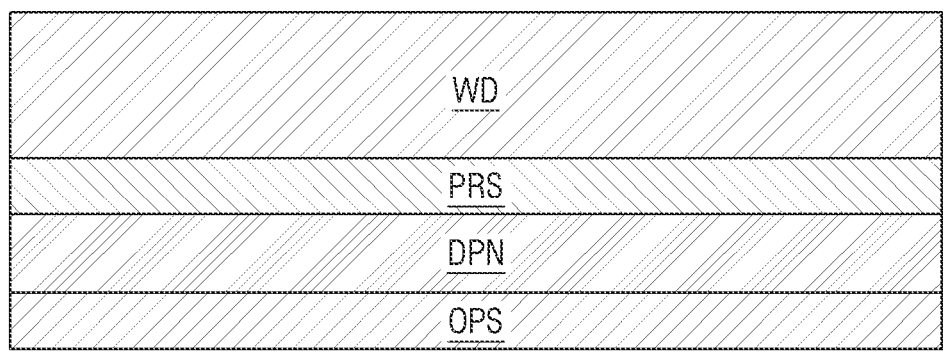
FIG. 16 is a schematic cross-sectional view illustrating a stacked relationship between a display panel and sensors in the display device according to one exemplary embodiment.

FIG. 16 is a schematic cross-sectional view illustrating a stacked relationship between a display panel and sensors in a display device according to one exemplary embodiment.

Referring to FIG. 16, the display device may include a display panel DPN, a pressure sensor PRS disposed above the display panel DPN, a window member WD disposed above the pressure sensor PRS, and an optical sensor OPS disposed below the display panel DPN. The display panel DPN, the pressure sensor PRS, the window member WD, and the optical sensor OPS may overlap each other in a thickness direction thereof. The exemplary embodiment of FIG. 16 illustrates the case in which the display panel DPN, the pressure sensor PRS, the window member WD, and the optical sensor OPS have the same width, side surfaces thereof are aligned with each other, and entire surfaces thereof overlap each other, but the present disclosure is not limited thereto, and, in one or more exemplary embodiments, some members may protrude from the side surfaces of the other members in a plan view.

A light emission direction of the display panel DPN may be an upward direction. The window member WD is disposed above the display panel DPN, which is a direction in which a display surface of the display panel DPN faces. The window member WD may be made of a transparent material such as a glass, a thin-film or an ultra-thin glass, or a transparent polymer such as a transparent polyimide.

The pressure sensor PRS may be disposed between the display panel DPN and the window member WD. The pressure sensor PRS may be at least partially disposed in a display area DPA. In this case, in order to not interfere with light that is output from the display panel DPN, a transparent pressure sensor may be applied as the pressure sensor PRS. As described above, the transparent pressure sensor may be implemented by forming all of the electrode, the sensitive material, the modifying material, and the like, which constitute the pressure sensor PRS, with transparent materials.

The optical sensor OPS is disposed below the display panel DPN. The optical sensor OPS may be at least partially disposed in the display area DPA. The optical sensor OPS receives light reflected from the object OBJ on the window member WD. Accordingly, a light sensing-path needs to be secured in a section from the window member WD to the optical sensor OPS, and in addition to the window member WD and the pressure sensor PRS, the display panel DPN, which is disposed in the middle of the light sensing-path, may also include a light transmission part (e.g., see "TA" in FIG. 36). The light transmission part of the display panel DPN may be implemented by a display light-transmission area (e.g., see "DPA_T" in FIG. 35). A detailed structure in which the display panel DPN forms the display light-transmission area will be described below.

Figure 17:
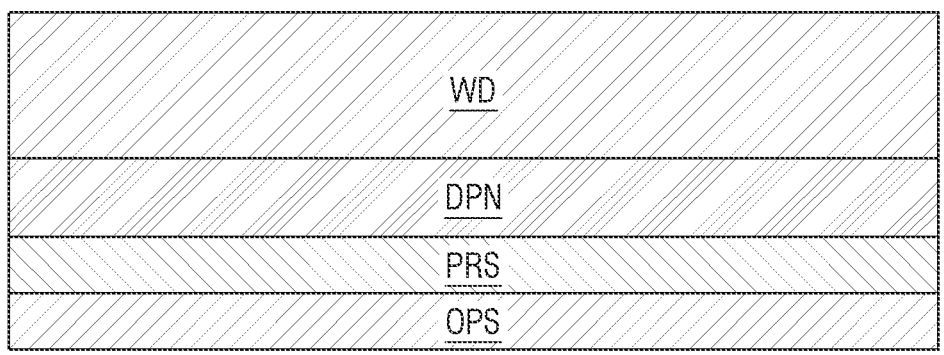
FIG. 17 is a schematic cross-sectional view illustrating a stacked relationship between a display panel and sensors in the display device according to another exemplary embodiment.

FIG. 17 is a schematic cross-sectional view illustrating a stacked relationship between a display panel and sensors in a display device according to another exemplary embodiment.

Referring to FIG. 17, the display device according to the illustrated exemplary embodiment is different from that of the exemplary embodiment described with reference to FIG. 16 in that a pressure sensor PRS is disposed between a display panel DPN and an optical sensor OPS.

In one or more exemplary embodiments, a window member WD is disposed on (e.g., directly on) the display panel DPN. The pressure sensor PRS is disposed below the display panel DPN. The optical sensor OPS is disposed below the pressure sensor PRS. Both the optical sensor OPS and the pressure sensor PRS may be at least partially disposed in a display area DPA.

The optical sensor OPS receives light reflected from the object OBJ on the window member WD. In the case of the illustrated exemplary embodiment, because the optical sensor OPS is disposed at the relatively lowermost portion, the display panel DPN and the pressure sensor PRS may be disposed on a light sensing-path that leads to the optical sensor OPS. Accordingly, in the case of the illustrated exemplary embodiment, the display panel DPN and the transparent pressure sensor PRS, which include a light transmission part, may be applied.

Figure 18:
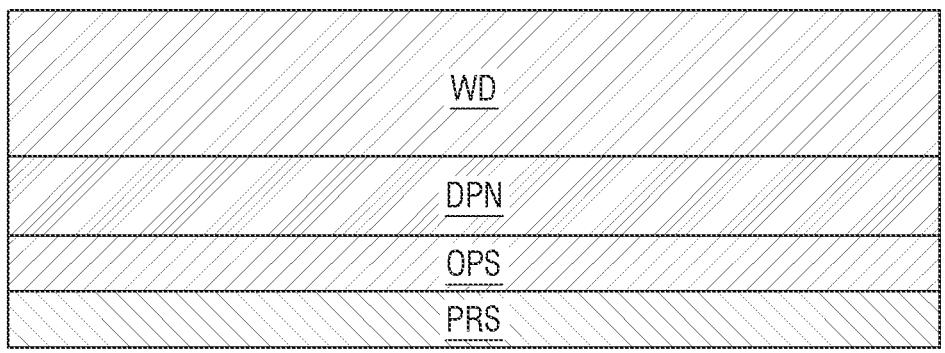
FIG. 18 is a schematic cross-sectional view illustrating a stacked relationship between a display panel and sensors in a display device according to still another exemplary embodiment.

FIG. 18 is a schematic cross-sectional view illustrating a stacked relationship between a display panel and sensors in a display device according to still another exemplary embodiment.

Referring to FIG. 18, the display device according to the illustrated exemplary embodiment is different from that of the exemplary embodiment described with reference to FIG. 17 in that an optical sensor OPS is disposed below a display panel DPN, and a pressure sensor PRS is disposed below the optical sensor OPS.

Specifically, the optical sensor OPS and the pressure sensor PRS are sequentially disposed below the display panel DPN. For example, the optical sensor OPS is disposed between the display panel DPN and the pressure sensor PRS. The optical sensor OPS receives light reflected from the object OBJ on a window member WD, and the display panel DPN, which is placed on a light sensing-path, may include a light transmission part. Meanwhile, the pressure sensor PRS is disposed below the optical sensor OPS and is not disposed on the light output path of the display panel DPN or the light sensing-path of the optical sensor OPS. Thus, in the case of the illustrated exemplary embodiment, an opaque pressure sensor PRS may be applied. However, the present disclosure is not limited thereto, and even in the case of the illustrated exemplary embodiment, a transparent pressure sensor PRS may be applied.

Figure 19:
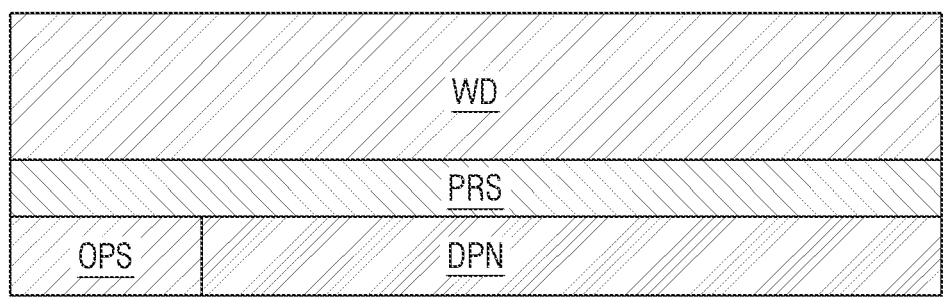
FIG. 19 is a schematic cross-sectional view illustrating a stacked relationship between a display panel and sensors in a display device according to yet another exemplary embodiment.

FIG. 19 is a schematic cross-sectional view illustrating a stacked relationship between a display panel and sensors in a display device according to yet another exemplary embodiment.

Referring to FIG. 19, the display device according to the illustrated exemplary embodiment illustrates that a display panel DPN and an optical sensor OPS may not overlap each other in a thickness direction.

Specifically, the optical sensor OPS is disposed outside the display panel DPN. The optical sensor OPS and the display panel DPN may be disposed on or at substantially the same layer due to a stacked structure (e.g., as illustrated in the embodiment of FIG. 19), but the present disclosure is not limited thereto. A pressure sensor PRS and a window member WD are sequentially disposed above the display panel DPN and the optical sensor OPS. Each of the pressure sensor PRS and the window member WD overlaps the display panel DPN and the optical sensor OPS in the thickness direction. The pressure sensor PRS may include a first region, in which the pressure sensor PRS overlaps the display panel DPN, and a second region in which the pressure sensor PRS overlaps the optical sensor OPS. The first region and the second region of the pressure sensor PRS may not overlap each other (e.g., in a thickness direction as illustrated in the embodiment of FIG. 19). The first region of the pressure sensor PRS may be formed to be transparent so as not to interfere with light that is output from the display panel DPN, and the second region of the pressure sensor PRS may be placed on a light sensing-path, which is for the optical sensor OPS to sense light, and thus may be formed to be transparent. Accordingly, a transparent pressure sensor PRS, which is entirely transparent including the first region and the second region, may be applied as the pressure sensor PRS.

Meanwhile, in the case of the illustrated exemplary embodiment, because the display panel DPN does not overlap the optical sensor OPS in the thickness direction, the display panel DPN is not placed on the light sensing-path of the optical sensor OPS. Thus, the display panel DPN may not include a separate light transmission part for light sensing.

Figure 20:
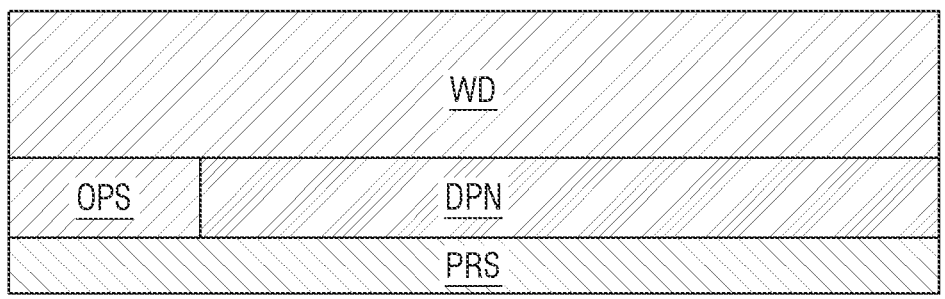
FIG. 20 is a schematic cross-sectional view illustrating a stacked relationship between a display panel and sensors in a display device according to still yet another exemplary embodiment.

FIG. 20 is a schematic cross-sectional view illustrating a stacked relationship between a display panel and sensors in a display device according to still yet another exemplary embodiment.

Referring to FIG. 20, the display device according to the illustrated exemplary embodiment is similar to that of the exemplary embodiment described with reference to FIG. 19 in that an optical sensor OPS is disposed outside a display panel DPN, but is different from that of the exemplary embodiment described with reference to FIG. 19 in that a pressure sensor PRS is disposed below the optical sensor OPS and the display panel DPN. A window member WD is disposed above the optical sensor OPS and the display panel DPN.

In the case of the illustrated exemplary embodiment, the pressure sensor PRS is not disposed on a light output path of the display panel DPN and a light sensing-path of the optical sensor OPS. Light output from the display panel DPN may be emitted to the outside through the window member WD. In addition, sensed light, which is reflected from the window member WD, may reach the optical sensor OPS through the window member WD. Thus, the display panel DPN does not need to include a light transmission part for securing the light sensing-path. In addition, the pressure sensor PRS is disposed at a relatively lower portion of the display device and thus is not positioned on the light output path of the display panel DPN or the light sensing-path of the optical sensor OPS. Thus, in the case of the illustrated exemplary embodiment, an opaque pressure sensor PRS may be applied.

Figure 21:
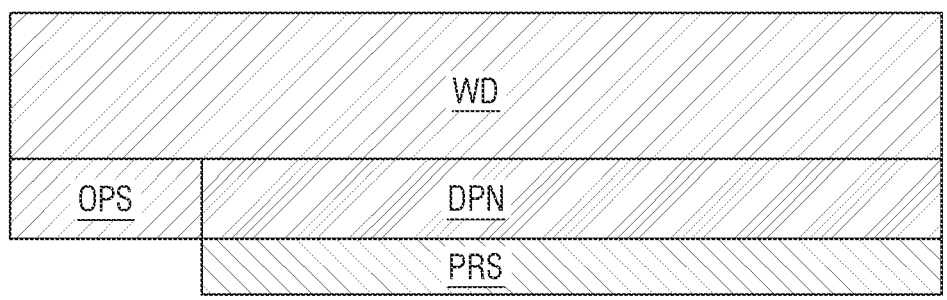
FIG. 21 is a schematic cross-sectional view illustrating a stacked relationship between a display panel and sensors in a display device according to still yet another exemplary embodiment.

FIG. 21 is a schematic cross-sectional view illustrating a stacked relationship between a display panel and sensors in a display device according to still yet another exemplary embodiment.

Referring to FIG. 21, the display device according to the illustrated exemplary embodiment is similar to that of the exemplary embodiment described with reference to FIG. 20 in that an optical sensor OPS is disposed outside a display panel DPN and a pressure sensor PRS is disposed below the display panel DPN but is different from that of the exemplary embodiment described with reference to FIG. 20 in that the pressure sensor PRS does not overlap the optical sensor OPS in a thickness direction.

As described above, in order for the pressure sensor PRS and the optical sensor OPS to be utilized in the blood pressure measuring module, it is desirable to sense light reflected from the object OBJ in a state in which the pressure of the object OBJ is recognized. In order to accurately sense the pressure by the object OBJ, the pressure sensor PRS may be positioned close to a touch point of the object OBJ. When the pressure sensor PRS and the optical sensor OPS overlap each other in the thickness direction, the pressure at the touch point may be easily measured, and even though the pressure sensor PRS and the optical sensor OPS do not overlap each other, when the pressure sensor PRS is positioned within a distance of about 50 mm, preferably about 30 mm in a horizontal direction with respect to the optical sensor OPS, significant pressure information may be obtained. Accordingly, as illustrated in FIG. 21, the sensors PRS and OPS may be utilized for the blood pressure measuring module by arranging the optical sensor OPS and the pressure sensor PRS in a non-overlapping manner and adjusting the horizontal separation distance between the optical sensor OPS and the pressure sensor PRS within about 50 mm or about 30 mm.

Figure 22:
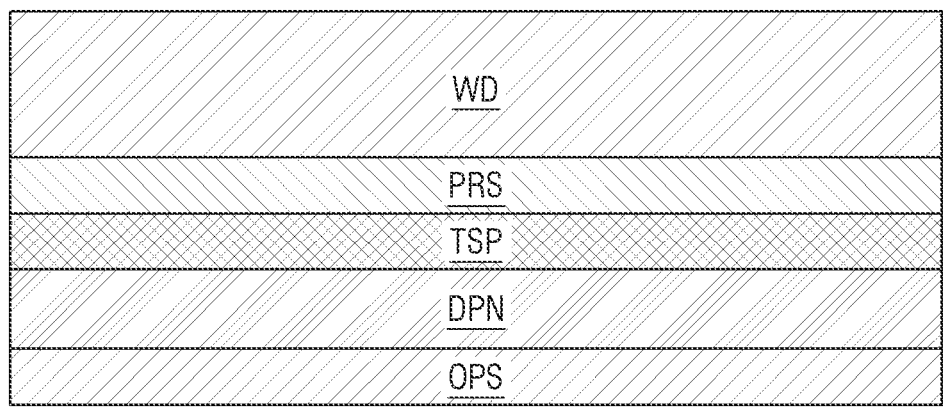
FIG. 22 is a schematic cross-sectional view illustrating a stacked relationship between a display panel and sensors in a display device according to still yet another exemplary embodiment.

FIG. 22 is a schematic cross-sectional view illustrating a stacked relationship between a display panel and sensors in a display device according to still yet another exemplary embodiment. FIG. 22 illustrates a case in which a touch member TSP is provided as a separate member instead of being installed to be included in a display panel DPN.

Referring to FIG. 22, the touch member TSP is disposed above the display panel DPN, a pressure sensor PRS is disposed above the touch member TSP, and a window member WD is disposed above the pressure sensor PRS. The touch member TSP may be provided in a rigid panel, flexible panel, or film type. An optical sensor OPS is disposed below the display panel DPN. The illustrated exemplary embodiment is different from the exemplary embodiment described with reference to FIG. 16 in that the touch member TSP is disposed between the display panel DPN and the pressure sensor PRS. In one or more exemplary embodiments, unlike the illustrated exemplary embodiment of FIG. 22, the pressure sensor PRS may be disposed on the display panel DPN, and the touch member TSP may be disposed above the pressure sensor PRS. In addition, the exemplary embodiments described with reference to FIGS. 17-21 may also be modified to have the structure in which the touch member TSP is disposed between the display panel DPN and the window member WD, as in the illustrated exemplary embodiment, and in the case of the exemplary embodiment described with reference to FIG. 19, the touch member TSP may be disposed above or below the pressure sensor PRS.

FIGS. 23-28 are layouts of display devices according to one or more exemplary embodiments. FIGS. 23-28 illustrate various planar arrangements of applicable display panel DPN and sensors PRS and OPS.

Referring to FIGS. 23-28, the pressure sensor PRS and the optical sensor OPS may have various planar arrangements (e.g., arrangements in a plan view) in relation to the display panel DPN in the display device.

Figure 23:
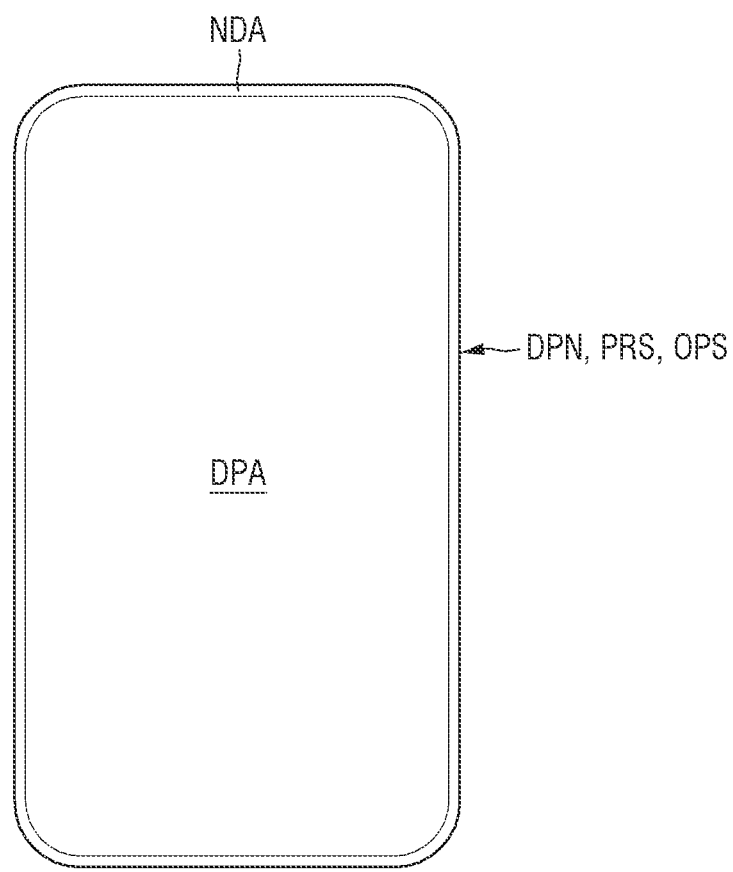
FIGS. 23-28 are layouts of display devices according to one or more exemplary embodiments.

For example, as illustrated in FIG. 23, each of the pressure sensor PRS and the optical sensor OPS may have substantially the same size as the display panel DPN in a plan view and may overlap each other (e.g., in a thickness direction). The exemplary embodiments described above with reference to FIGS. 16-18 may have such a planar arrangement, but the present disclosure is not limited thereto. In one or more exemplary embodiments, the pressure sensor PRS and the optical sensor OPS may entirely cover the display area DPA of the display panel DPN but may protrude or be recessed from each other in the non-display area NDA in a plan view. In one or more exemplary embodiments, the pressure sensor PRS and/or the optical sensor OPS overlap in the entire display area DPA but may not overlap in the entire non-display area NDA.

Figure 24:
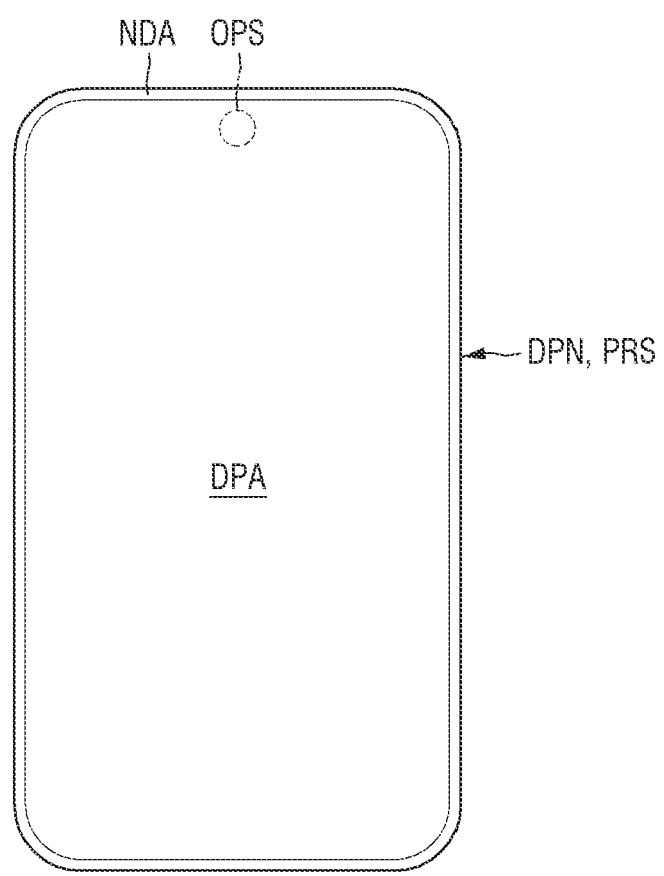

As another example, as illustrated in FIG. 24, the pressure sensor PRS may have a size that is substantially equal to that of the display panel DPN in a plan view, but the optical sensor OPS may be disposed to overlap only some regions of the display panel DPN. For example, as illustrated in the drawings, the optical sensor OPS may be disposed to overlap some regions of the display area DPA of the display panel DPN or overlap some regions of the non-display area NDA. When the optical sensor OPS has a relatively small size (or smaller size) in a plan view as compared with the display panel DPN or the pressure sensor PRS in the exemplary embodiments described with reference to FIGS. 16-18, the exemplary embodiments described with reference to FIGS. 16-18 may have the same planar arrangement as FIG. 24.

Figure 25:
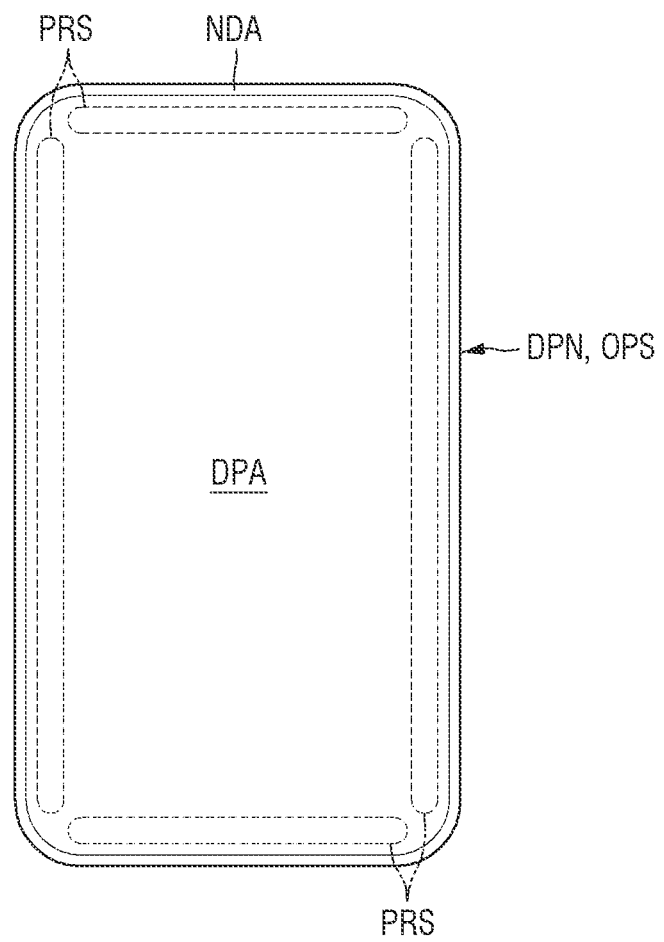

As still another example, as illustrated in FIG. 25, the optical sensor OPS has a size that is substantially equal to that of the display panel DPN in a plan view, but the pressure sensor PRS has a size smaller than that of the display panel DPN and is disposed to overlap only some regions of the display panel DPN. In one or more exemplary embodiments, as illustrated in the drawings, the pressure sensor PRS may be disposed to overlap some regions of the display area DPA of the display panel DPN or overlap some regions of the non-display area NDA. When the pressure sensor PRS has a relatively small size as compared with the display panel DPN or the optical sensor OPS in the exemplary embodiments described with reference to FIGS. 16-18, the exemplary embodiments described with reference to FIGS. 16-18 may have the same planar arrangement as FIG. 25.

Figure 26:
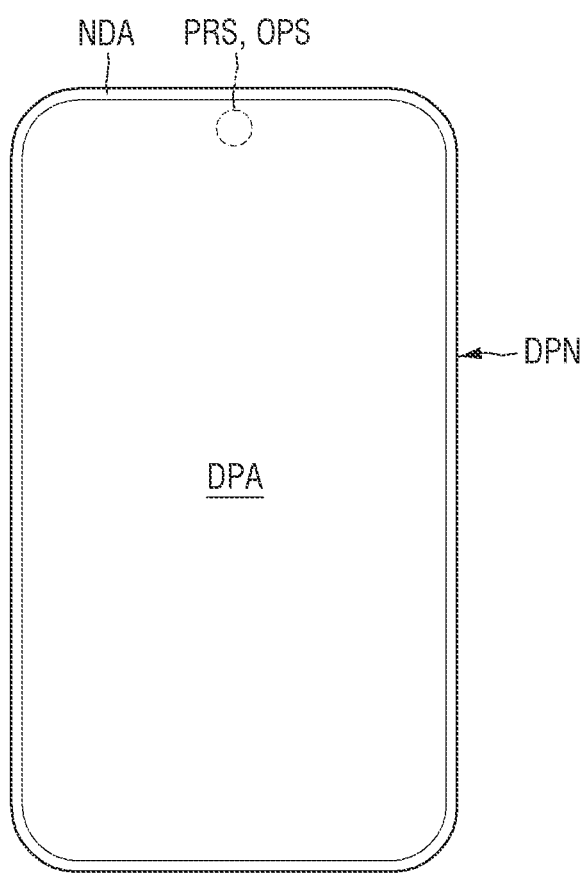

As yet another example, as illustrated in FIG. 26, the pressure sensor PRS and the optical sensor OPS may have a size smaller than that of the display panel DPN and may be disposed to overlap only some regions of the display panel DPN. In one or more exemplary embodiments, as illustrated in the drawings, the pressure sensor PRS and the optical sensor OPS may be disposed to overlap some regions of the display area DPA of the display panel DPN or overlap some regions of the non-display area NDA. In FIG. 26, the pressure sensor PRS and the optical sensor OPS are illustrated as having the same size (e.g., the same size in a plan view) and completely overlapping each other, but the present disclosure is not limited thereto, and either one of those two may be larger than the other one. When the pressure sensor PRS and the optical sensor OPS have a relatively small size as compared with the display panel DPN or the optical sensor OPS in the exemplary embodiments described with reference to FIGS. 16-18, the exemplary embodiments described with reference to FIGS. 16-18 may have the same planar arrangement as FIG. 26.

Figure 27:
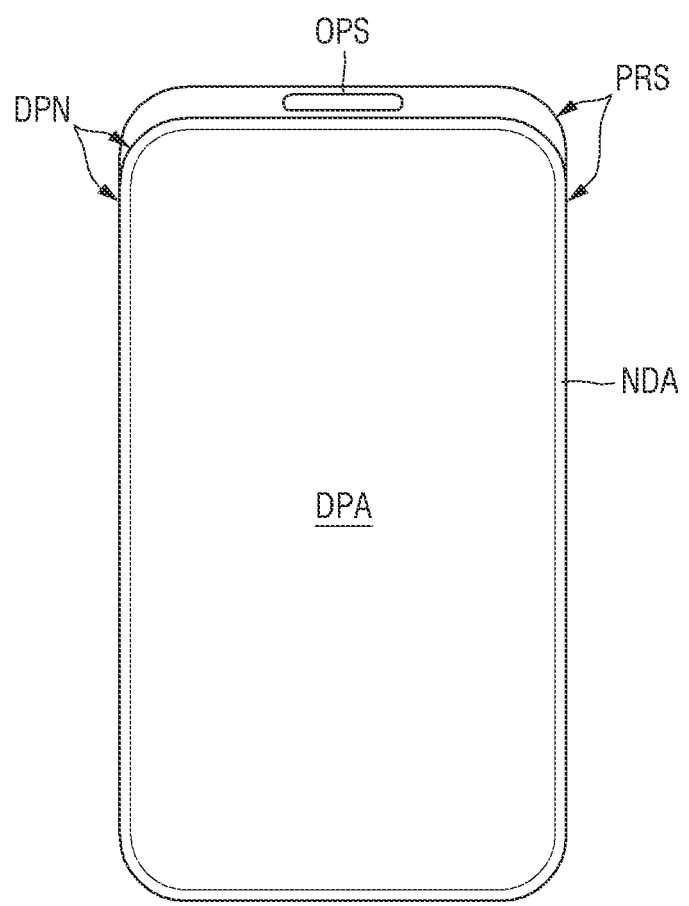

As still yet another example, as illustrated in FIG. 27, the optical sensor OPS may be disposed outside of one side of the display panel DPN and may not overlap the display panel DPN and the pressure sensor PRS, and the pressure sensor PRS may be disposed to cover both the display panel DPN and the optical sensor OPS. The exemplary embodiments described with reference to FIGS. 19 and 20 may have such a planar arrangement.

Figure 28:
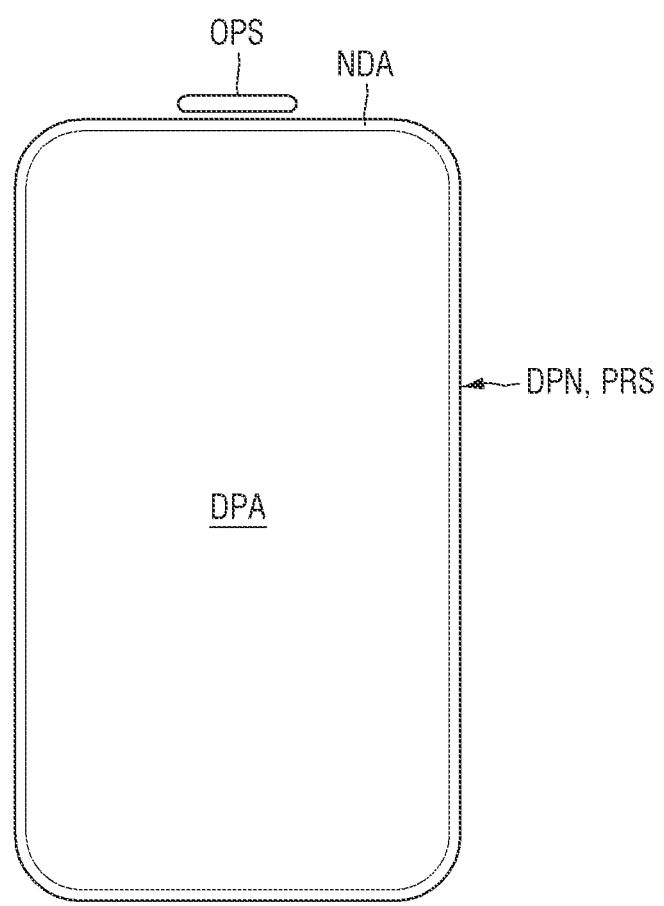

As still yet another example, as illustrated in FIG. 28, the pressure sensor PRS may have a size that is substantially equal to that of the display panel DPN in a plan view, and the optical sensor OPS may be disposed along one side of the display panel DPN and may not overlap the display panel DPN and the pressure sensor PRS. The exemplary embodiment described with reference to FIG. 21 may have such a planar arrangement. In the case of the illustrated exemplary embodiment, the pressure sensor PRS and the optical sensor OPS do not overlap each other, but as described above, significant pressure information for the blood pressure measurement may be obtained by positioning the optical sensor OPS at a distance of about 50 mm or less, and preferably about 30 mm or less, from the pressure sensor PRS.

Figure 29:
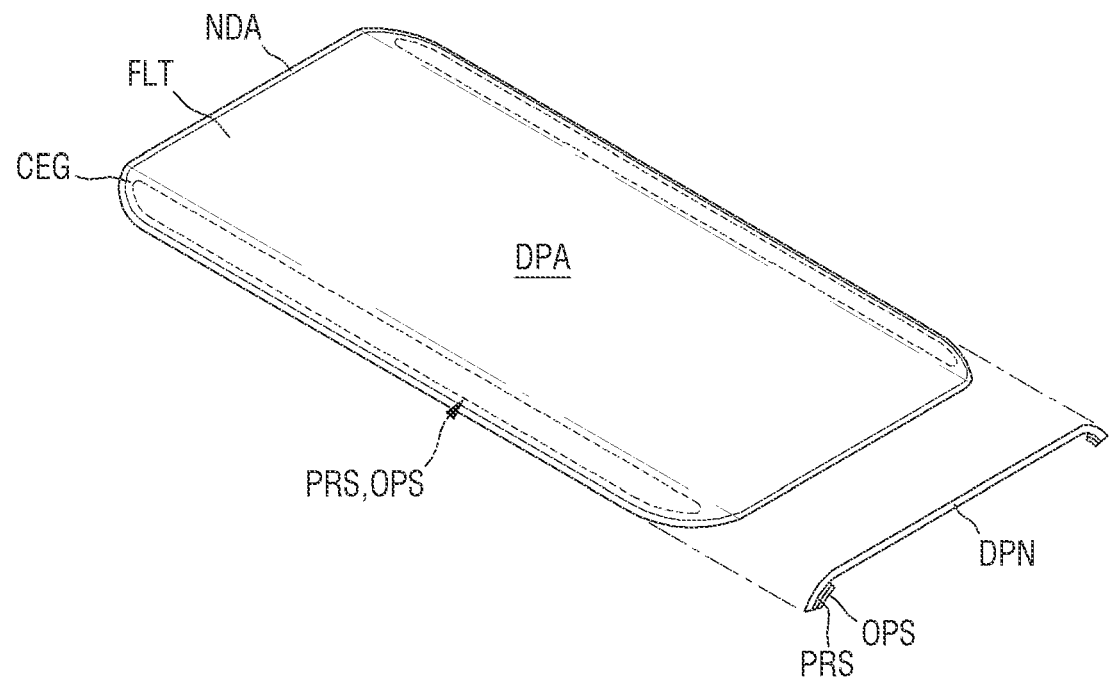
FIG. 29 is a perspective view of a display device according to still another exemplary embodiment.

FIG. 29 is a perspective view of a display device according to still another exemplary embodiment. Referring to FIG. 29, it is illustrated that some edges of the display device according to the illustrated exemplary embodiment may have a curved surface.

Referring to FIG. 29, a long side edge of the display device may have a curved surface that is convexly curved in a rear surface direction. The edge with a curved surface (hereinafter, referred to as a curved edge CEG) may include a display area DPA, but at least some regions of the curved edge CEG may include a non-display area NDA. In some exemplary embodiments, the pressure sensor PRS may be disposed to overlap the curved edge CEG. The pressure sensor PRS may not overlap a flat surface portion FLT of the display device or may be disposed only up to the vicinity of a boundary between the curved edge CEG and the flat surface portion FLT. The optical sensor OPS is disposed to overlap or to be adjacent to the pressure sensor PRS. Specifically, the optical sensor OPS may overlap the curved edge CEG or may be positioned at a distance within about 50 mm or about 30 mm from the boundary between the curved edge CEG and the flat surface portion FLT.

Figure 30:
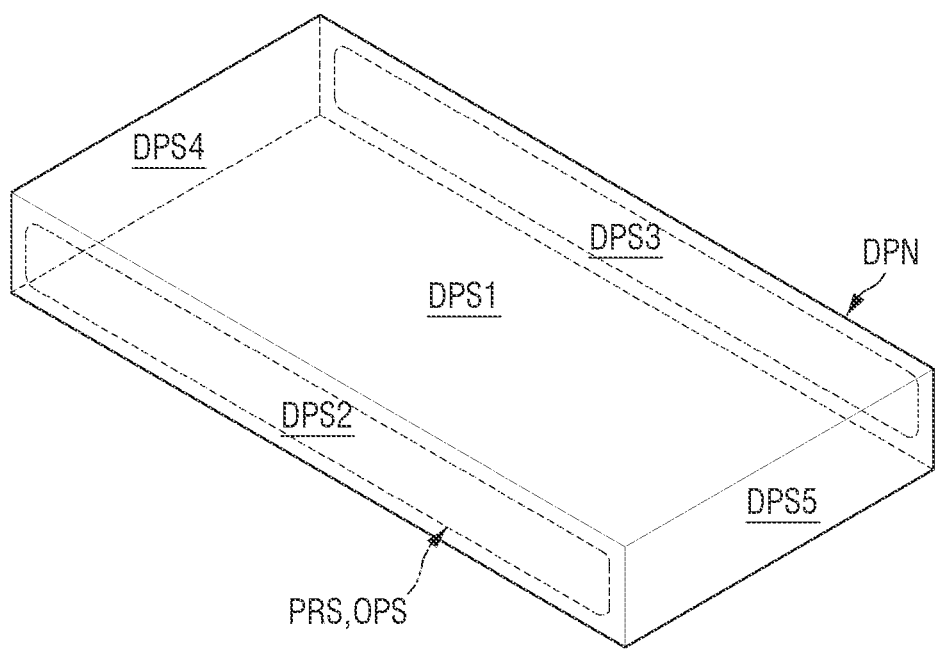
FIG. 30 is a perspective view of a display device according to yet another exemplary embodiment.
Figure 31:
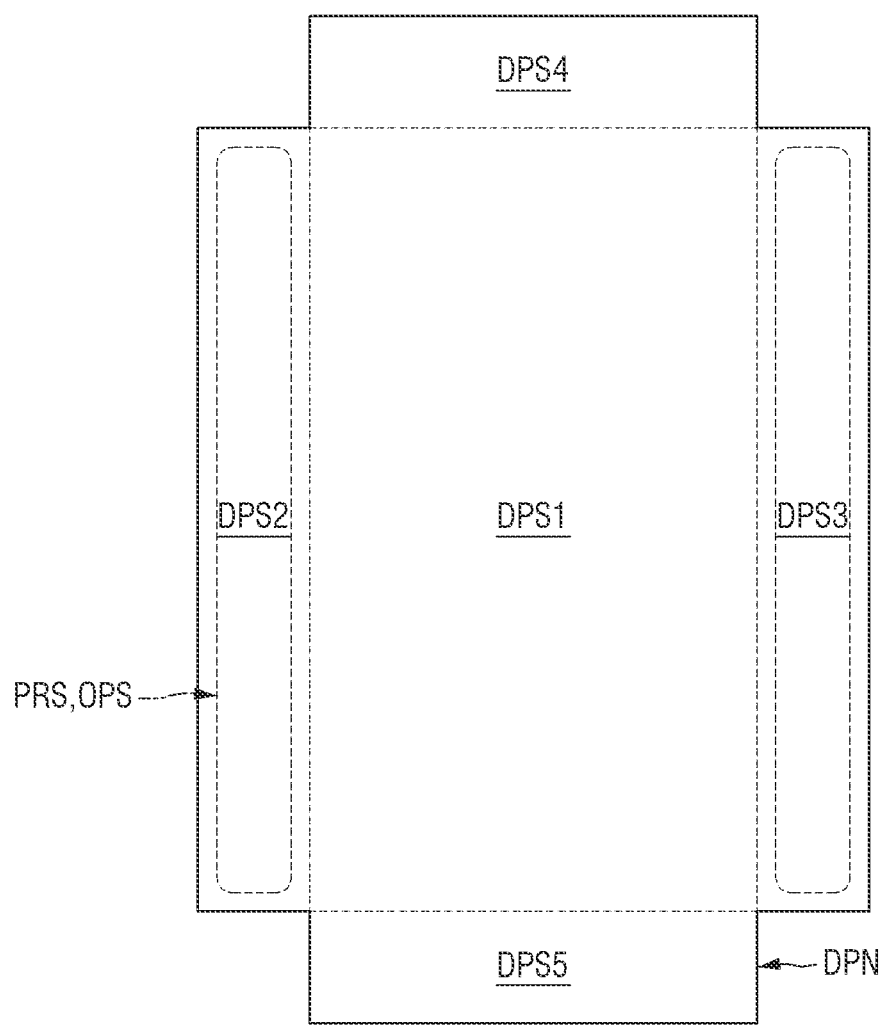
FIG. 31 is an exploded view of the display device of FIG. 30.

FIG. 30 is a perspective view of a display device according to yet another exemplary embodiment. FIG. 31 is an exploded view of the display device of FIG. 30. The exemplary embodiment described with reference to FIGS. 30 and 31 illustrate that the display device may be applied as a stereoscopic display device.

Referring to FIGS. 30 and 31, the display device may include a plurality of display surfaces DPS1, DPS2, DPS3, DPS4, and DPS5 that are positioned on different planes. In the display device that has a rectangular parallelepiped shape, a first display surface DPS1 may be disposed on one surface (upper surface) of the display device, a second display surface DPS2 and a third display surface DPS3 may be disposed on side surfaces of the display device which are adjacent to long sides of the display device, respectively, and a fourth display surface DPS4 and a fifth display surface DPS5 may be disposed on side surfaces of the display device which are adjacent to short sides of the display device, respectively. In one exemplary embodiment, the first display surface DPS1 is a flat surface, and the second to fifth display surfaces DPS2 to DPS5 have a flat surface that is perpendicular to the first display surface DPS1. However, the present disclosure is not limited thereto, and the second to fifth display surfaces DPS2 to DPS5 may have angles other than that perpendicular to the first display surface DPS1 or may have a curved surface shape such as the curved edge CEG of FIG. 29.

A pressure sensor PRS and an optical sensor OPS may be variously disposed in a suitable manner in the display device. As a non-limiting example specialized in a stereoscopic display device, the pressure sensor PRS and the optical sensor OPS may be disposed to be adjacent to at least one of the second to fifth display surfaces DPS2 to DPS5. In this case, the pressure sensor PRS and the optical sensor OPS may be disposed to face side surfaces of the display device.

Figure 32:
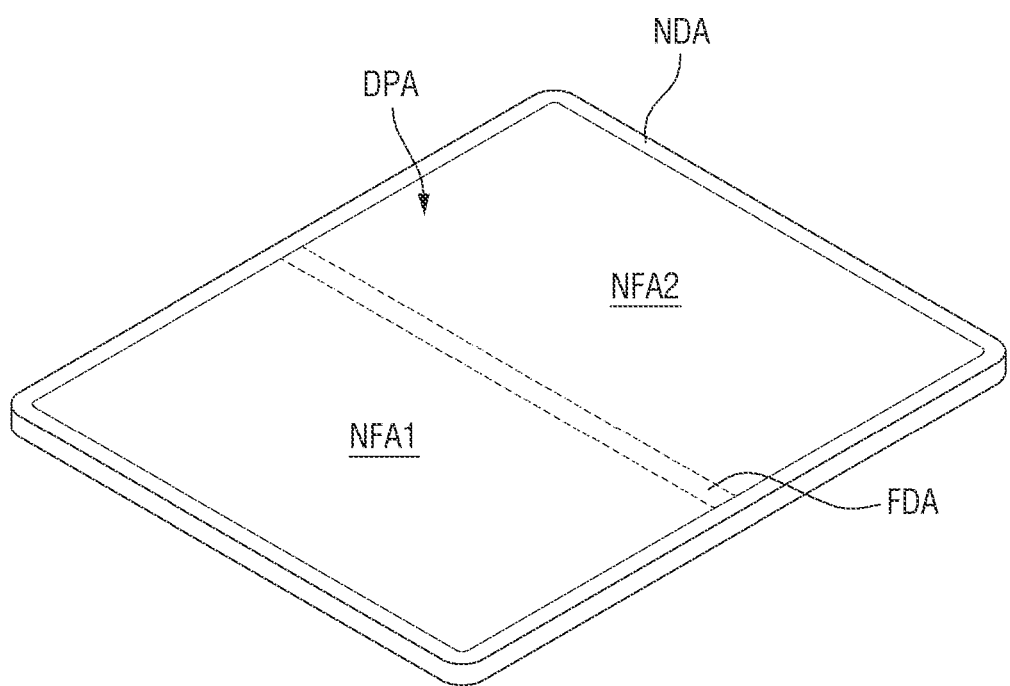
FIG. 32 is a perspective view of a display device according to still yet another exemplary embodiment.
Figure 33:
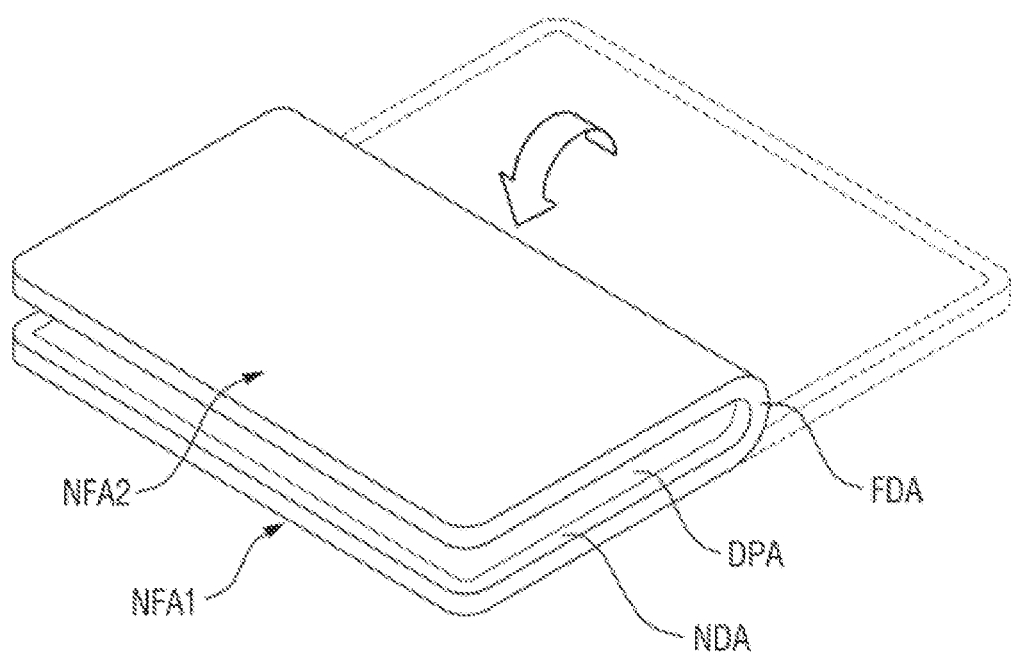
FIG. 33 is a perspective view illustrating a state in which the display device of FIG. 32 is folded.

FIG. 32 is a perspective view of a display device according to still yet another exemplary embodiment. FIG. 33 is a perspective view illustrating a state in which the display device of FIG. 32 is folded. FIGS. 32 and 33 illustrate that the display device may be a foldable display device. The term "foldable display device" used in the present specification refers to a display device capable of folding and is interpreted as including a device capable of having both a folded state and a non-folded state as well as a device in a fixed folded state. Further, the folded state typically includes being folded at an angle of about 180°, but the present disclosure is not limited thereto, and the state may be understood as being the folded state even when the folded angle is greater than or less than 180°, for example, the folded angle is more than 90° and less than 180° or more than 120° and less than 180°. Moreover, when the display device is in a state of being bent out of the non-folded state, it may be referred to as the folded state even when the folding is not completely performed. For example, when the maximum folded angle is 90° or more, it may be expressed as being in the folded state to be distinguished from the non-folded state even when the display device is bent at an angle of 90° or less. The radius of curvature when folded may be about 5 mm or less, and preferably, in the range of about 1 mm to about 2 mm, or about 1.5 mm, but the present disclosure is not limited thereto.

Referring to FIGS. 32 and 33, the display device may be folded based on a folding line FDA (or a folding shaft). The folding line FDA may have a straight line shape that extends in one direction in a plan view. Although the case in which the folding line FDA extends parallel to a short side of the display device is illustrated in the drawing, the present disclosure is not limited thereto, and the folding line FDA may be parallel to a long side of the display device or may be tilted with respect to the short side and the long side.

In one exemplary embodiment, the folding line FDA of the display device may be fixed at a specific position. In the display device, one or more folding lines FDA may be provided at the specific position. In another exemplary embodiment, the positions of the folding lines FDA are not specified in the display device and may be freely set in various suitable regions.

The display device may be divided into a first non-folded area NFA1 and a second non-folded area NFA2 on the basis of the folding line FDA. The first non-folded area NFA1 may be positioned on one side of the folding line FDA, and the second non-folded area NFA2 may be positioned on the other side of the folding line FDA. When the folding line FDA is fixed at the specific position, the first non-folded area NFA1 and the second non-folded area NFA2 may be specified as areas in which the folding is not performed. The specified first non-folded area NFA1 and second non-folded area NFA2 may have the same width, but the present disclosure is not limited thereto. When the folding line FDA is not specified, the first non-folded area NFA1 and the second non-folded area NFA2 may have different areas depending on the position in which the folding line FDA is set.

A display area DPA of the display device may be disposed over both the first non-folded area NFA1 and the second non-folded area NFA2. Furthermore, the display area DPA may also be positioned on the folding line FDA that corresponds to a boundary between the first non-folded area NFA1 and the second non-folded area NFA2. That is, the display area DPA of the display device may be disposed continuously or substantially continuously regardless of boundaries between the non-folded areas NFA1 and NFA2, the folding lines FDA, and the like. However, the present disclosure is not limited thereto, and the display area DPA may be disposed in the first non-folded area NFA1 but may not be disposed in the second non-folded area NFA2, and the display area DPA may be disposed in the first non-folded area NFA1 and the second non-folded area NFA2 but the non-display part NDA may not be disposed in the folding line FDA.

In one exemplary embodiment, a pressure sensor PRS and an optical sensor OPS may be disposed in the first non-folded area NFA1 or the second non-folded area NFA2. However, the present disclosure is not limited thereto, and the pressure sensor PRS and/or the optical sensor OPS may overlap the folding line FDA that corresponds to the boundary between the first non-folded area NFA1 and the second non-folded area NFA2. When the pressure sensor and the optical sensor have the planar arrangement as illustrated in FIG. 23, the pressure sensor and the optical sensor may be disposed over all of the first non-folded area NFA1, the folding line FDA, and the second non-folded area NFA2.

The display device may be folded by an in-folding method which is folded such that display surfaces face each other while facing inward or may be folded by an out-folding method which is folded such that the display surfaces face outward (e.g., face away from each other). The display device may be folded by only one of the in-folding method and the out-folding method (e.g., one-way folding), or both the in-folding and the out-folding (e.g., two-way folding) may be performed. In the case of the display device in which both the in-folding and the out-folding are performed, the in-folding and the out-folding may be performed on the basis of the same or single folding line FDA, or the display device may include a plurality of folding lines FDA such as an in-folding dedicated folding line and an out-folding dedicated folding line, in which different types of folding are performed. For example, the display device is folded toward different directions about the in-folding dedicated folded line and the out-folded dedicated folding line.

In one exemplary embodiment, a display panel DPN and a layer, a panel, and a substrate that are stacked on the display panel DPN have their own flexible characteristics (e.g., are flexible) so that corresponding members may all be folded, and thus the display device may be folded. In some exemplary embodiments, at least some of the display panel or the members stacked on the display panel DPN may have a shape that is separated on the basis of the folding line FDA. In this case, the separated members that are positioned in the non-folded area may not have flexible characteristics.

Meanwhile, the display device illustrated in FIG. 32 may further include a window member. The window member, which is applied to the foldable display device, may be made of a foldable material. For example, the window member may include a polymer such as transparent polyimide, which itself has flexible characteristics (e.g., is flexible) or may be made of ultra-thin glass so that the window member may be folded. In the case of ultra-thin glass, the ultra-thin glass may have a thickness of about 0.2 mm or less, preferably about 0.1 mm or less, and more preferably about 0.07 mm or less. Even in the case of polyimide, the polyimide may be applied in a thin thickness of about 0.1 mm or about 0.05 mm or less to reduce folding stress.

Figure 34:
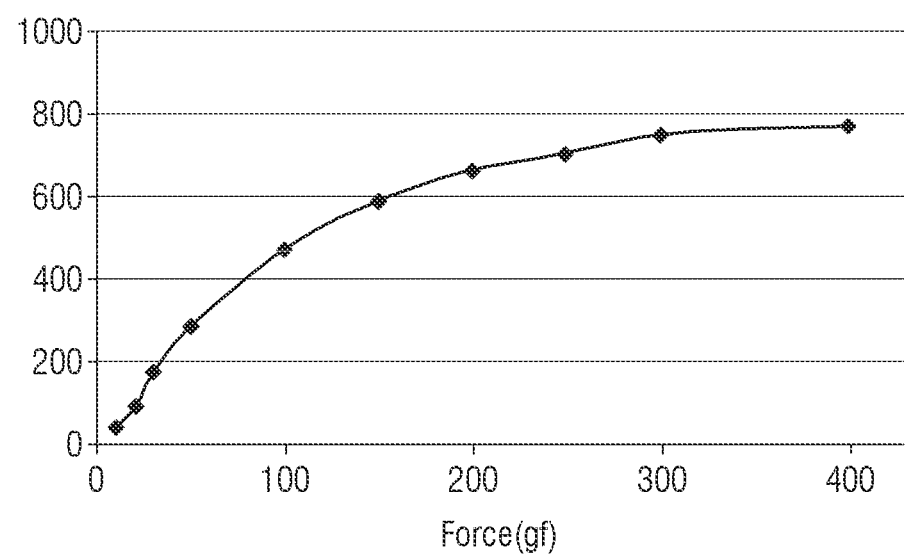
FIG. 34 is a graph illustrating a relationship between pressure and electrical resistance in a pressure sensor of the display device according to one exemplary embodiment.

Because the window member with a thin thickness is applied to the foldable display device as described above, more accurate pressure sensing is possible. Reference is made to FIG. 34 for a detailed description thereof.

FIG. 34 is a graph illustrating a relationship between pressure and electrical resistance in the pressure sensor of the display device according to one exemplary embodiment. FIG. 34 illustrates a result of measuring the electrical resistance according to pressure for a display device in which an ultra-thin glass with a thickness of about 0.2 mm is applied as a window member and a force sensor is disposed below a display panel as the pressure sensor. In FIG. 34, an X-axis represents a pressing force, and a Y-axis represents a relative magnitude for a reciprocal of the electrical resistance that is measured by the force sensor.

Referring to FIG. 34, the reciprocal of the electrical resistance tends to increase as the pressure increases. That is, as the pressure increases, the electrical resistance decreases. Meanwhile, the change in the electrical resistance due to the pressure occurs concurrently (e.g., simultaneously) with pressurization without excessive threshold. Accordingly, the corresponding pressure may be estimated precisely from the relative value of the corresponding reciprocal of the electrical resistance for every pressure in the range of about 0 gf to about 400 gf. The pressure of about 0 gf to about 400 gf corresponds to about 0 mHg to about 300 mHg when converted to a blood pressure, and thus, all the pressure ranges desirable for a blood pressure measurement may be covered.

In the display device described above, the pressure sensor PRS may be mounted on the display panel DPN, coupled to the display panel DPN, or provided integrally with the display panel DPN. The pressure sensor PRS may be attached to the display panel DPN through a coupling layer that includes a resin layer, an adhesive layer, and the like. In some exemplary embodiments, the pressure sensor PRS may also be integrated into the display panel DPN. For example, the pressure sensor PRS may be formed (e.g., directly formed) on the display panel DPN or may be mounted on the display panel DPN in the form of a chip, a printed circuit board, a film, and/or the like. A pressure driving part configured to drive the pressure sensor PRS and sense may be disposed inside the pressure sensor PRS, but may be mounted on the display panel DPN or a printed circuit board, which is connected to the display panel DPN, in the form of a separate driving integrated circuit (IC). As another example, the pressure driving part may be provided in the form of a chip that is integrated with a control part of the blood pressure measuring module or a driving part such as a data driver IC or a touch driver IC that is provided in the display panel DPN.

Hereinafter, the structure of a light transmission part TA of the display panel DPN will be described in more detail. As described above, in the display device according to some exemplary embodiments, the display panel DPN is placed on the light sensing-path of the optical sensor OPS, and the light transmission part TA may be included to sufficiently secure the amount of light received by the optical sensor OPS. The light transmission part TA may be secured by forming the structure of the display panel DPN to be different from those of other areas.

Figure 35:
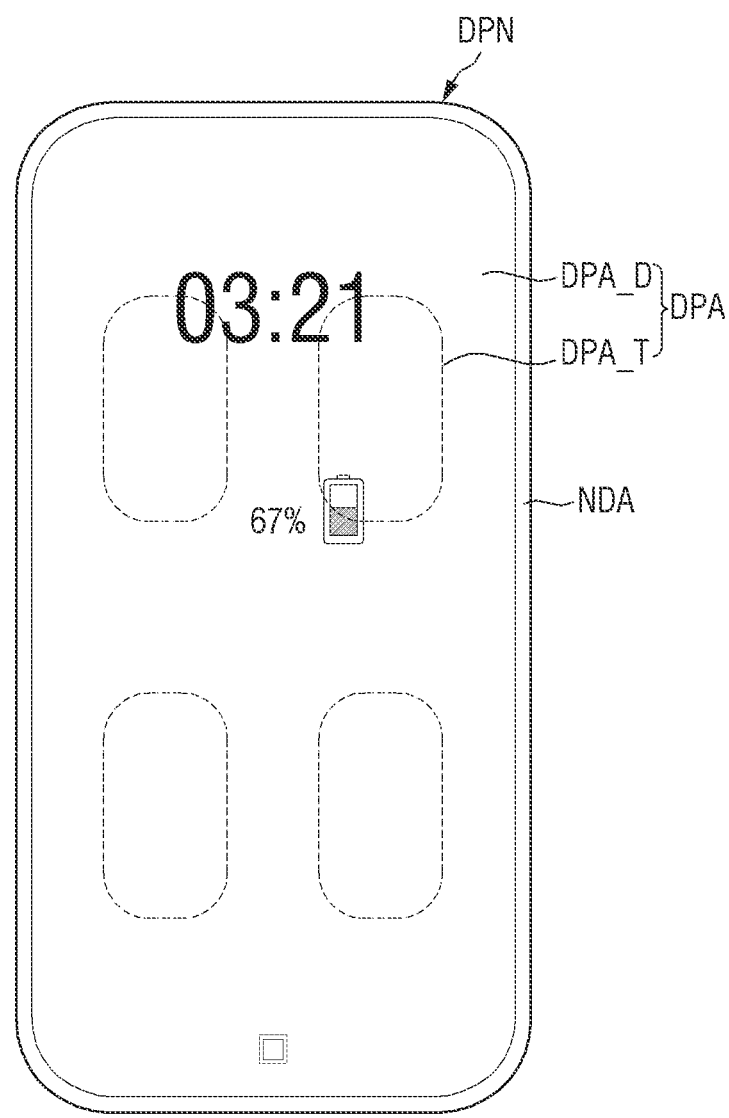
FIG. 35 is a plan layout of a display area of a display panel according to one exemplary embodiment.
Figure 36:
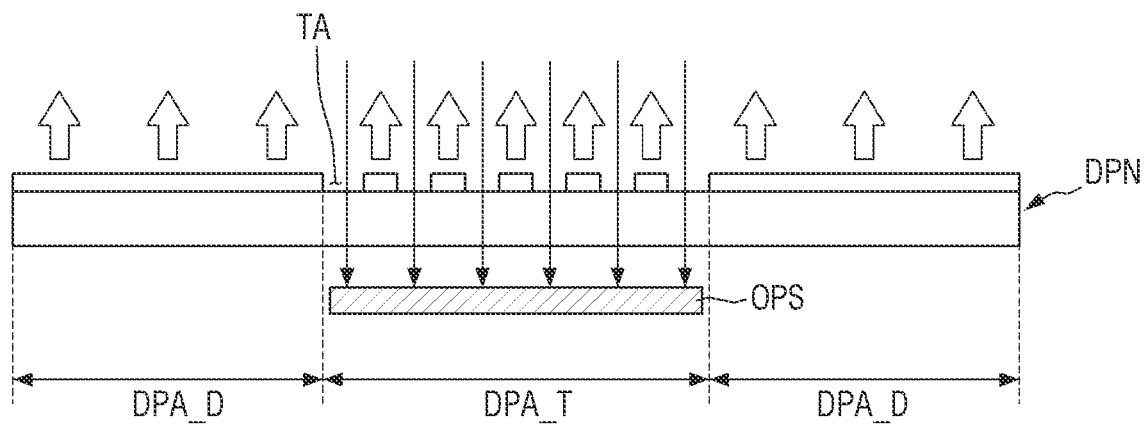
FIG. 36 is a cross-sectional view of the display panel of FIG. 35.

FIG. 35 is a plan layout of a display area of a display panel according to one exemplary embodiment. FIG. 36 is a cross-sectional view of the display panel of FIG. 35.

Referring to FIGS. 35 and 36, a display area DPA of a display panel DPN may include a light transmission part TA. The display area DPA of the display panel DPN may include a display light-transmission area DPA_T that is a first display area that includes the light transmission part TA. The display light-transmission area DPA_T is an area in which an emission area (e.g., "EMA" in FIG. 39) of a pixel PX and the light transmission part TA are mixed. The light transmission part TA of the display light-transmission area DPA_T is an area that does not emit light itself but may transmit light in a thickness direction thereof. The light may include light having a visible light wavelength as well as light having near-infrared and/or infrared wavelengths. The light, which is transmitted through the light transmission part TA, may further include light having near-ultraviolet and/or ultraviolet wavelengths.

One display light-transmission area DPA_T may include a plurality of light transmission parts TA that are separated from each other. The emission area of the pixel PX may be disposed between the light transmission parts TA. The emission area of the pixel PX and the light transmission part TA may not be visually distinguished in the display light-transmission area DPA_T. The light transmission part TA of the display light-transmission area DPA_T is an area that does not emit light itself but may transmit light in a thickness direction thereof. The light may include light having a visible light wavelength as well as light having near-infrared and/or infrared wavelengths. The light, which is transmitted through the light transmission part TA, may further include light having near-ultraviolet and/or ultraviolet wavelengths.

The display area DPA of the display panel DPN may further include a display-only area DPA_D that is a second display area that does not include the light transmission part TA. That is, the display area DPA of the display panel DPN may be divided into the display light-transmission area DPA_T and the display-only area DPA_D.

The display area DPA may include one display light-transmission area DPA_T and may also include a plurality of display light-transmission areas DPA_T that are separated from each other. The display-only area DPA_D may be disposed around the display light-transmission area DPA_T. The display-only area DPA_D may partially or entirely surround the display light-transmission area DPA_T. The display-only area DPA_D and the display light-transmission area DPA_T may be adjacent to each other and may be continuously or substantially continuously disposed without separate physical distinction. In one exemplary embodiment, the display-only area DPA_D and the display light-transmission area DPA_T may not be visually distinguished, but the present disclosure is not limited thereto.

There is no restriction on an arrangement region of the display light-transmission area DPA_T within the display area DPA. For example, the display light-transmission area DPA_T may be disposed in a central region of the display area DPA, which is spaced apart from the non-display area NDA. As another example, the display light-transmission area DPA_T may be disposed around an edge of the display area DPA and disposed in contact with or in proximity to the non-display area NDA.

Figure 39:
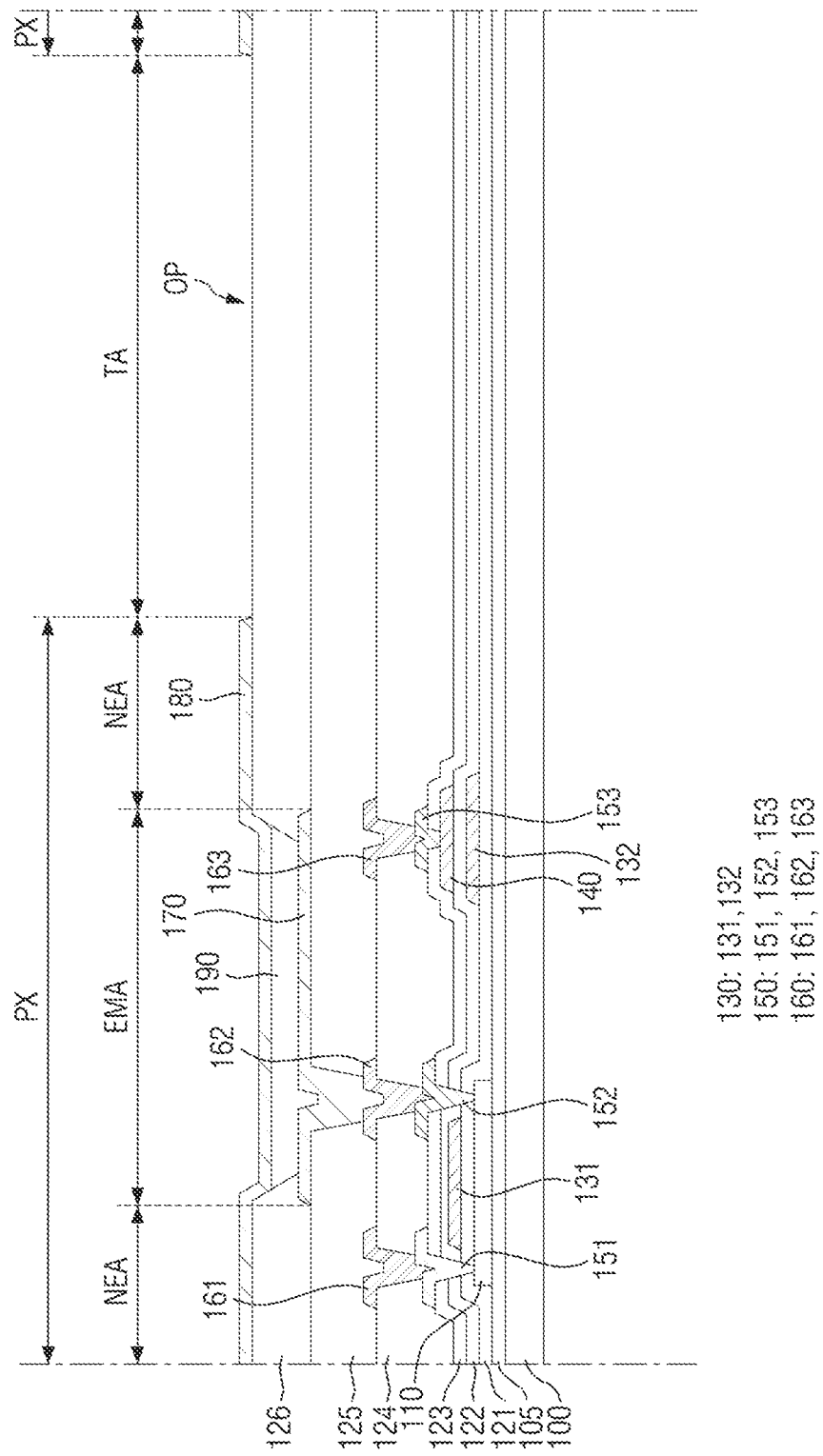
FIG. 39 is a cross-sectional view illustrating a pixel and a light transmission part of a display panel according to some exemplary embodiments.

A non-emission area (e.g., "NEA" in FIG. 39) of the display-only area DPA_D or the display light-transmission area DPA_T is also an area which does not emit light itself, but the light transmission part TA has a light transmittance greater than that of the non-emission area (e.g., "NEA" in FIG. 39). Here, the light transmittance is a transmittance of light that passes through each area and refers to a transmittance of light that travels in a thickness direction of each area. Accordingly, the display light-transmission area DPA_T, which includes the light transmission part TA, has a light transmittance greater than that of the display-only area DPA_D.

As described above, the display light-transmission area DPA_T may be used as a light sensing-path. An optical sensor OPS of a blood pressure measuring module may be disposed to overlap the display light-transmission area DPA_T.

Furthermore, the display light-transmission area DPA_T may be utilized as an optical path for other optical members other than the blood pressure measuring module. For example, a camera, an infrared proximity sensor, an iris recognition sensor, a fingerprint sensor, and/or the like may be disposed to overlap the display light-transmission area DPA_T to obtain light desirable for the operation thereof. The optical sensor OPS of the blood pressure measuring module and the remaining sensors described above may also be implemented by one common member or different independent members. When a plurality of members are used for light sensing, the corresponding members may be disposed to be adjacent to each other or spaced apart from each other at different positions. The plurality of independent members may be arranged together in one grouped display light-transmission area DPA_T or may be disposed in the display light-transmission areas DPA_T, which are separated from each other, respectively.

In the above-described sensors, the amount of light required may be different for each sensor depending on the type thereof. When the plurality of sensors require different amounts of light, an aperture ratio (ratio of the light transmission part TA to the total area) of the corresponding display light-transmission area DPA_T and the light transmittance of the light transmission part TA may also be adjusted accordingly. For example, the transmittance of light that passes through the light transmission part TA may be controlled by adjusting an area of the light transmission part TA to the total area of the display light-transmission area DPA_T or adjusting a stacked structure or a material in a thickness direction thereof so that it is possible to appropriately or suitably design light transmittance per unit area and the total light transmission amount (average light transmittance×area) of the entire display light-transmission area DPA_T.

Figure 37:
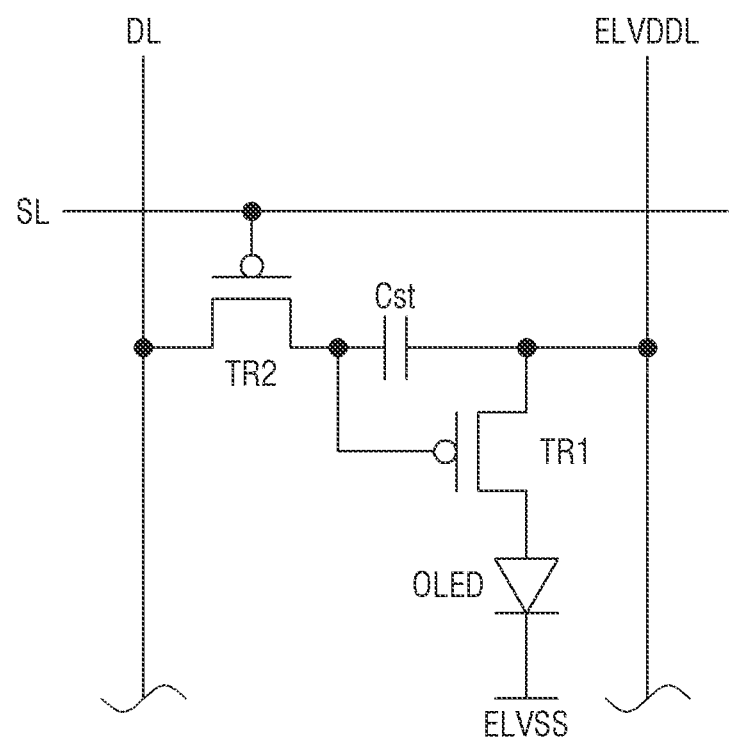
FIG. 37 is a circuit diagram of one pixel of the display device according to one exemplary embodiment.

FIG. 37 is a circuit diagram of one pixel of the display device according to one exemplary embodiment.

Referring to FIG. 37, a pixel circuit may include a first transistor TR1, a second transistor TR2, a capacitor Cst, and an organic light-emitting diode (OLED). A scan line SL, a data line DL, and a first power voltage line ELVDDL are connected to each pixel circuit.

The first transistor TR1 may be a driving transistor, and the second transistor TR2 may be a switching transistor. Although both of the first transistor TR1 and the second transistor TR2 are illustrated in the drawing as being p-channel metal-oxide-semiconductor (PMOS) transistors, any one or both of the first transistor TR1 and the second transistor TR2 may be an n-channel metal-oxide-semiconductor (NMOS) transistor with suitable changes to other circuit elements as appreciated by one of ordinary skill in the art.

A first electrode (source electrode) of the first transistor TR1 is connected to the first power voltage line ELVDDL, and a second electrode (drain electrode) thereof is connected to an anode electrode of the OLED. A first electrode (source electrode) of the second transistor TR2 is connected to the data line DL, and a second electrode (drain electrode) thereof is connected to a gate electrode of the first transistor TR1. The capacitor Cst is connected between the gate electrode and the first electrode of the first transistor TR1. A cathode electrode of the OLED receives a second power voltage ELVSS. The second power voltage ELVSS may be lower than a first power voltage ELVDD that is provided from the first power voltage line ELVDDL.

The second transistor TR2 may output a data signal, which is applied to the data line DL, in response to a scan signal that is applied to the scan line SL. The capacitor Cst may be charged with a voltage corresponding to the data signal that is received from the second transistor TR2. The first transistor TR1 may control a driving current that flows through the OLED in accordance with electric charges stored in the capacitor Cst.

An equivalent circuit of FIG. 37 is merely one exemplary embodiment, and the pixel circuit may include a greater number of transistors and/or capacitors. For example, in other embodiments, the pixel circuit may include 7 transistors.

Figure 38:
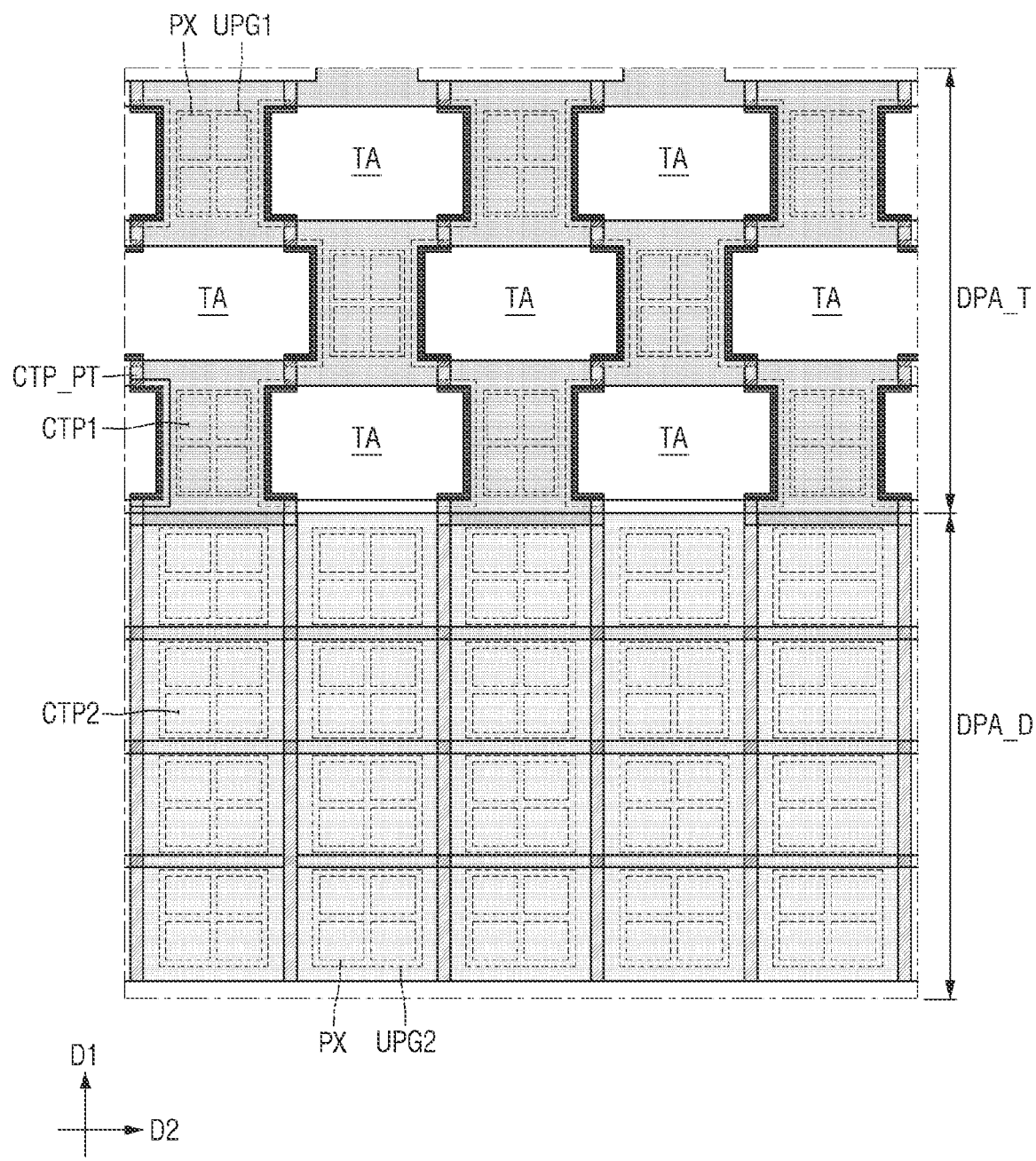
FIG. 38 is a plan layout of a display light-transmission area and a display-only area of the display panel according to one exemplary embodiment.

FIG. 38 is a plan layout of a display light-transmission area and a display-only area of the display panel according to one exemplary embodiment.

Referring to FIG. 38, a display light-transmission area DPA_T includes a plurality of pixels PX and a plurality of light transmission parts TA. The light transmission parts TA and the pixels PX are mixed (e.g., adjacent to each other in the display light-transmission area DPA_T). Although the light transmission part TA may be mixed with every one pixel PX, a plurality of pixels PX (e.g., four pixels) may be gathered in a unit group (hereinafter referred to as a "first unit-pixel group UPG1"), and the light transmission part TA may be disposed between the first unit-pixel groups UPG1. The four pixels PX may include, for example, a red pixel, a green pixel, a blue pixel, and a green pixel, but the present disclosure is not limited thereto.

The combined area of the first unit-pixel group UPG1 and the light transmission part TA that is adjacent to the first unit-pixel group UPG1 may be substantially equal to the area of eight pixels PX in a display-only area DPA_D. When it is defined that four pixels PX also form a unit group (hereinafter referred to as a "second unit-pixel group UPG2") in the display-only area DPA_D, the combined area of the first unit-pixel groups UPG1 and one light transmission part TA of the display light-transmission area DPA_T may be substantially equal to the combined area of two second unit-pixel groups UPG2 of the display-only area DPA_D.

The display light-transmission area DPA_T may have a smaller (or lesser) number of pixels PX or a smaller size of the pixels PX than the display-only area DPA_D within the same area because of the area occupied by the light transmission parts TA. In other words, a unit area of the display-only area DPA_D may have more available space for pixels PX than an equivalent unit area of the display light-transmission area DPA_T because the display light-transmission area DPA_T accommodates light transmission parts TA in addition to pixels PX. As described above, when the combined area of the first unit-pixel group UPG1 and one light transmission part TA of the display light-transmission area DPA_T is equal or substantially equal to the combined area of the two second unit-pixel groups UPG2 of the display-only area DPA_D, the display light-transmission area DPA_T may exhibit about half the resolution of the display-only area DPA_D in the same area.

An average width of rows and columns, which are formed by the first unit-pixel groups UPG1 and the light transmission parts TA in the display light-transmission area DPA_T, may be substantially equal to an average width of rows and columns, which are formed by the second unit-pixel groups UPG2 in the display-only area DPA_D, respectively, but the present disclosure is not limited thereto. The first unit-pixel groups UPG1 and the light transmission parts TA in the display light-transmission area DPA_T may be alternately arranged along a second direction D2 (row extension direction) in one row. In rows that are adjacent to each other, the first unit-pixel group UPG1 and the light transmission part TA may be alternately arranged in the display light-transmission area DPA_T along a first direction D1 (column extension direction).

The relative size of the first unit-pixel group UPG1 and the light transmission part TA in the display light-transmission area DPA_T may be variously modified in a suitable manner according to the amount of light required by the sensor that is disposed to overlap the display light-transmission area DPA_T. In one exemplary embodiment in which a sufficient amount of light is required, the size of the light transmission part TA may be greater than the size of the first unit-pixel group UPG1 of the display light-transmission area DPA_T. In this case, the size of each pixel PX in the display light-transmission area DPA_T may be smaller than the size of each pixel PX in the display-only area DPA_D. In one exemplary embodiment, the width of the light transmission part TA in the second direction D2 may be greater than the width of the first unit-pixel group UPG1 in the second direction D2.

In one exemplary embodiment, the cathode electrode may not be disposed in the light transmission part TA in the entire display area DPA. For example, the cathode electrode may be disposed in the entire remaining display area DPA other than the light transmission parts TA. That is, the light transmission part TA may be defined by whether or not the cathode electrode is disposed. When viewed based on the cathode electrode (e.g., the locations of the cathode electrode in a plan view), the light transmission part TA may correspond to a cathode electrode hole.

In one or more exemplary embodiments, in an area other than the light transmission part TA, the cathode electrode may be formed of a plurality of electrode layers. For example, a separate cathode electrode pattern may be disposed for each unit-pixel group, and the cathode electrode patterns may be electrically connected to each other by overlapping or being in contact with each other at the boundary of the unit-pixel groups that are adjacent to each other. Such a structure may be a result of depositing the cathode electrode two or more times.

Second cathode electrode patterns CTP2, which are disposed in each second unit-pixel group UPG2 in the display-only area DPA_D, may each have a rectangular shape. The second cathode electrode patterns CTP2, which are adjacent to each other, may overlap each other at edge portions thereof.

Meanwhile, first cathode electrode patterns CTP1, which are disposed in each of the first unit-pixel groups UPG1 in the display light-transmission area DPA_T, may each have an "I" shape that has a narrow central portion and two longer ends in the first direction D1 based on a width in the second direction D2. The two ends of the first cathode electrode pattern CTP1 in the first direction D1 may include protrusions that protrude from the center portion. The width of the center portion of the first cathode electrode pattern CTP1 in the second direction D2 may be smaller than the width of the second cathode electrode pattern CTP2 in the second direction D2, and the widths of the two ends of the first cathode electrode pattern CTP1 in the second direction D2 may be substantially equal to the width of the second cathode electrode pattern CTP2 in the second direction D2, but the present disclosure is not limited thereto. In the display light-transmission area DPA_T, protrusions CTP_PT at two ends of the first cathode electrode pattern CTP1 may overlap the protrusions CTP_PT of another first cathode electrode pattern CTP1 that is diagonally adjacent to the first cathode electrode patterns CTP1.

A thin-film transistor and also a power line or a data line may not be disposed in the light transmission parts TA of the display light-transmission area DPA_T. The data line and the power line, which extend in the first direction D1, may extend to bypass the light transmission part TA. In addition, an insulating film may also be partially removed (or partially omitted) from the light transmission part TA as compared to other areas of the display area DPA. The transmittance of the light transmission part TA varies according to the stacked structure of the light transmission part TA, and thus various stacking structures may be designed in consideration of required transmittance, process efficiency, planar size of the light transmission part TA, and the like. Hereinafter, the structure of the pixel PX and the light transmission part TA will be described in detail through a cross-sectional structure of the display panel DPN.

FIG. 39 is a cross-sectional view illustrating a pixel and a light transmission part of a display panel according to some exemplary embodiments.

In FIG. 39, among two transistors of FIG. 38, the first transistor TR1 is illustrated in the form of a thin-film transistor, and the second transistor TR2 is not illustrated.

First, a cross-sectional structure of a pixel PX will be described in detail with reference to FIG. 39. A display panel DPN may include a substrate 100, a buffer layer 105, a semiconductor layer 110, a first insulating layer 121, a first conductive layer 130, a second insulating layer 122, a second conductive layer 140, a third insulating layer 123, a third conductive layer 150, a fourth insulating layer 124, a fourth conductive layer 160, a fifth insulating layer 125, a fifth conductive layer 170, a pixel definition film 126 including an opening configured to expose the fifth conductive layer 170, an organic layer 190 disposed in the opening of the pixel definition film 126, and a sixth conductive layer 180 disposed on the pixel definition film 126 and the organic layer 190. Each of the above-described layers may be formed of a single film or may also be formed of a stacked film including a plurality of films. Another layer may be further disposed between the above-described layers.

The substrate 100 supports the respective layers disposed thereon. The substrate 100 may be made of an insulating material such as a polymer resin. Examples of the polymer material may include polyethersulphone (PES), polyacrylate (PA), polyarylate (PAR), polyetherimide (PEI), polyethylene napthalate (PEN), polyethylene terephthalate (PET), polyphenylene sulfide (PPS), polyallylate, polyimide (PI), polycarbonate (PC), cellulose triacetate (CAT), cellulose acetate propionate (CAP), or a combination thereof. The substrate 100 may be a flexible substrate that is bendable, foldable, and rollable. In one or more exemplary embodiments, the material forming the flexible substrate may include PI, but the present disclosure is not limited thereto.

The buffer layer 105 is disposed on the substrate 100. The buffer layer 105 may prevent or substantially prevent diffusion of impurity ions, prevent or substantially prevent permeation of moisture or ambient air, and perform a surface planarization function. The buffer layer 105 may include silicon nitride, silicon oxide, silicon oxynitride, or the like. The buffer layer 105 may be omitted according to the type of substrate 100, process conditions, and/or the like.

The semiconductor layer 110 is disposed on the buffer layer 105. The semiconductor layer 110 forms a channel of a thin-film transistor of the pixel PX. The semiconductor layer 110 may include polycrystalline silicon. However, the present disclosure is not limited thereto, and the semiconductor layer 110 may include monocrystalline silicon, low-temperature polycrystalline silicon, amorphous silicon, or an oxide semiconductor. The oxide semiconductor may include a binary compound (ABx), a ternary compound (ABxCy), or a quaternary compound (ABxCyDz), which contains indium, zinc, gallium, tin, titanium, aluminum, hafnium (Hf), zirconium (Zr), magnesium (Mg), and the like.

The first insulating layer 121 may be a gate insulating film that has a gate insulating function. The first insulating layer 121 may include a silicon compound, a metal oxide, or the like. For example, the first insulating layer 121 may include silicon oxide, silicon nitride, silicon oxynitride, aluminum oxide, tantalum oxide, hafnium oxide, zirconium oxide, titanium oxide, and/or the like. These may be used alone or in combination with each other. The first insulating layer 121 may be a single film or a multilayer film that includes a stacked film of different materials.

The first insulating layer 121 is disposed on the semiconductor layer 110 and may be generally disposed on an entire surface of the substrate 100. In one or more exemplary embodiments, the first insulating layer 121 covers most of the surface of the substrate 100.

The first conductive layer 130 is disposed on the first insulating layer 121. The first conductive layer 130 may be a first gate conductive layer. The first conductive layer 130 may include a gate electrode 131 of the thin-film transistor of the pixel PX, a scan line connected to the gate electrode 131, and a first storage capacitor electrode 132.

The first conductive layer 130 may include at least one metal selected from among molybdenum (Mo), aluminum (Al), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and copper (Cu). The first conductive layer 130 may be a single film or a multilayer film.

The second insulating layer 122 may be disposed on the first conductive layer 130. The second insulating layer 122 may be an interlayer insulating film. The second insulating layer 122 may include an inorganic insulating material such as silicon oxide, silicon nitride, silicon oxynitride, hafnium oxide, aluminum oxide, titanium oxide, tantalum oxide, and/or zinc oxide.

The second conductive layer 140 is disposed on the second insulating layer 122. The second conductive layer 140 may be a second gate conductive layer. The second conductive layer 140 may include a second storage capacitor electrode 140. The second conductive layer 140 may include one or more metals selected from among molybdenum (Mo), aluminum (Al), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and copper (Cu). The second conductive layer 140 may be made of the same material as the first conductive layer 130, but the present disclosure is not limited thereto. The second conductive layer 140 may be a single film or a multilayer film.

The third insulating layer 123 is disposed on the second conductive layer 140. The third insulating layer 123 may be an interlayer insulating film. The third insulating layer 123 may include an inorganic insulating material such as silicon oxide, silicon nitride, silicon oxynitride, hafnium oxide, aluminum oxide, titanium oxide, tantalum oxide, or zinc oxide, or an organic insulating material such as an acrylic resin (polyacrylate-based resin), an epoxy resin, a phenolic resin, a polyamide-based resin, a polyimide-based resin, an unsaturated polyester-based resin, a poly phenylenether-based resin, a polyphenylene sulfide-based resin, or benzocyclobutene (BCB). The third insulating layer 123 may be a single film or a multilayer film that includes a stacked film of different materials.

The third conductive layer 150 is disposed on the third insulating layer 123. The third conductive layer 150 may be a first source/drain conductive layer. The third conductive layer 150 may include a first electrode 151 and a second electrode 152 of the thin-film transistor of the pixel PX. The first electrode 151 and the second electrode 152 of the thin-film transistor may be electrically connected to a source region and a drain region of the semiconductor layer 110 through contact holes that pass through (or penetrate) the third insulating layer 123, the second insulating layer 122, and the first insulating layer 121. A first power voltage electrode 153 of the pixel PX may also be included in the third conductive layer 150.

The third conductive layer 150 may include one or more metals selected from among aluminum (Al), molybdenum (Mo), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and copper (Cu). The third conductive layer 150 may be a single film or a multilayer film. For example, the third conductive layer 150 may have a stacked structure of Ti/Al/Ti, Mo/Al/Mo, Mo/AlGe/Mo, Ti/Cu, or the like.

The fourth insulating layer 124 is disposed on the third conductive layer 150. The fourth insulating layer 124 covers the third conductive layer 150. The fourth insulating layer 124 may be a via layer. The fourth insulating layer 124 may include an organic insulating material such as an acrylic resin (polyacrylate-based resin), an epoxy resin, phenolic resin, a polyimide-based resin, a polyimide-based resin, an unsaturated polyester-based resin, a poly phenylenether-based resin, a polyphenylene sulfide-based resin, and/or benzocyclobutene (BCB).

The fourth conductive layer 160 is disposed on the fourth insulating layer 124. The fourth conductive layer 160 may be a second source/drain conductive layer. The fourth conductive layer 160 may include a data line, a connection electrode 162, and first power voltage lines 161 and 163 of the pixel PX. The first power voltage line 161 may be electrically connected to the first electrode 151 of the thin-film transistor of the pixel PX through a contact hole that passes through the fourth insulating layer 124 in the pixel PX. The connection electrode 162 may be electrically connected to the second electrode 152 of the thin-film transistor of the pixel PX through a contact hole that passes through the fourth insulating layer 124. The first power voltage line 163 may also be electrically connected to the first power voltage electrode 153 through a contact hole that passes through the fourth insulating layer 124.

The fourth conductive layer 160 may include at least one metal selected from among aluminum (Al), molybdenum (Mo), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and copper (Cu). The fourth conductive layer 160 may be a single film or a multilayer film. The fourth conductive layer 160 may be made of the same material as the third conductive layer 150, but the present disclosure is not limited thereto.

The fifth insulating layer 125 is disposed on the fourth conductive layer 160. The fifth insulating layer 125 covers the fourth conductive layer 160. The fifth insulating layer 125 may be a via layer. The fifth insulating layer 125 may include the same material as the fourth insulating layer 124 described above or may include at least one material selected from the exemplified materials that constitute the fourth insulating layer 124. The fourth conductive layer 160 may be omitted, and the same function may be performed by the third conductive layer 150.

The fifth conductive layer 170 is disposed on the fifth insulating layer 125. An anode electrode, which is a pixel electrode, may be formed of the fifth conductive layer 170. The anode electrode may be electrically connected to the connection electrode 162 formed of the fourth conductive layer 160 through a contact hole, which passes through the fifth insulating layer 125 and may be connected to the second electrode 152 of the thin-film transistor through the connection electrode 162. The anode electrode may at least partially overlap an emission area EMA of the pixel PX.

The fifth conductive layer 170 may have, but is not limited to, a stacked film structure formed by stacking a material layer having a high work function and a reflective material layer, wherein the material layer is made of one of indium tin oxide (ITO), indium zinc oxide (IZO), zinc oxide (ZnO), and indium oxide (In$_2$O$_3$), and the reflective material layer is made of one selected from silver (Ag), magnesium (Mg), aluminum (Al), platinum (Pt), lead (Pd), gold (Au), nickel (Ni), neodymium (Nd), iridium (Ir), chromium (Cr), lithium (Li), calcium (Ca), and mixtures thereof. The material layer, which has a high work function, may be disposed on the reflective material layer to be close to the organic layer 190. The fifth conductive layer 170 may have a multilayer structure of ITO/Mg, ITO/MgF, ITO/Ag, or ITO/Ag/ITO, but the present disclosure is not limited thereto.

The pixel definition film 126 may be disposed on the fifth conductive layer 170. The pixel definition film 126 may at least partially overlap a non-emission area NEA of the pixel PX. The pixel definition film 126 may have or define an opening configured to expose the fifth conductive layer 170. The pixel definition film 126 may include an inorganic insulating material such as silicon oxide, silicon nitride, silicon oxynitride, hafnium oxide, aluminum oxide, titanium oxide, tantalum oxide, or zinc oxide, and/or an organic insulating material such as an acrylic resin (polyacrylate-based resin), an epoxy resin, a phenolic resin, a polyamide-based resin, a polyimide-based resin, an unsaturated polyester-based resin, a poly phenylenether-based resin, a polyphenylene sulfide-based resin, or benzocyclobutene (BCB). The pixel definition film 126 may be a single film or a multilayer film that includes a stacked film of different materials.

The organic layer 190 is disposed in the opening of (i.e., the opening defined by) the pixel definition film 126. The organic layer 190 may include an organic light-emitting layer, a hole injection/transport layer, and an electron injection/transport layer. The organic layer 190 may overlap the emission area EMA (e.g., in a thickness direction).

Figure 40:
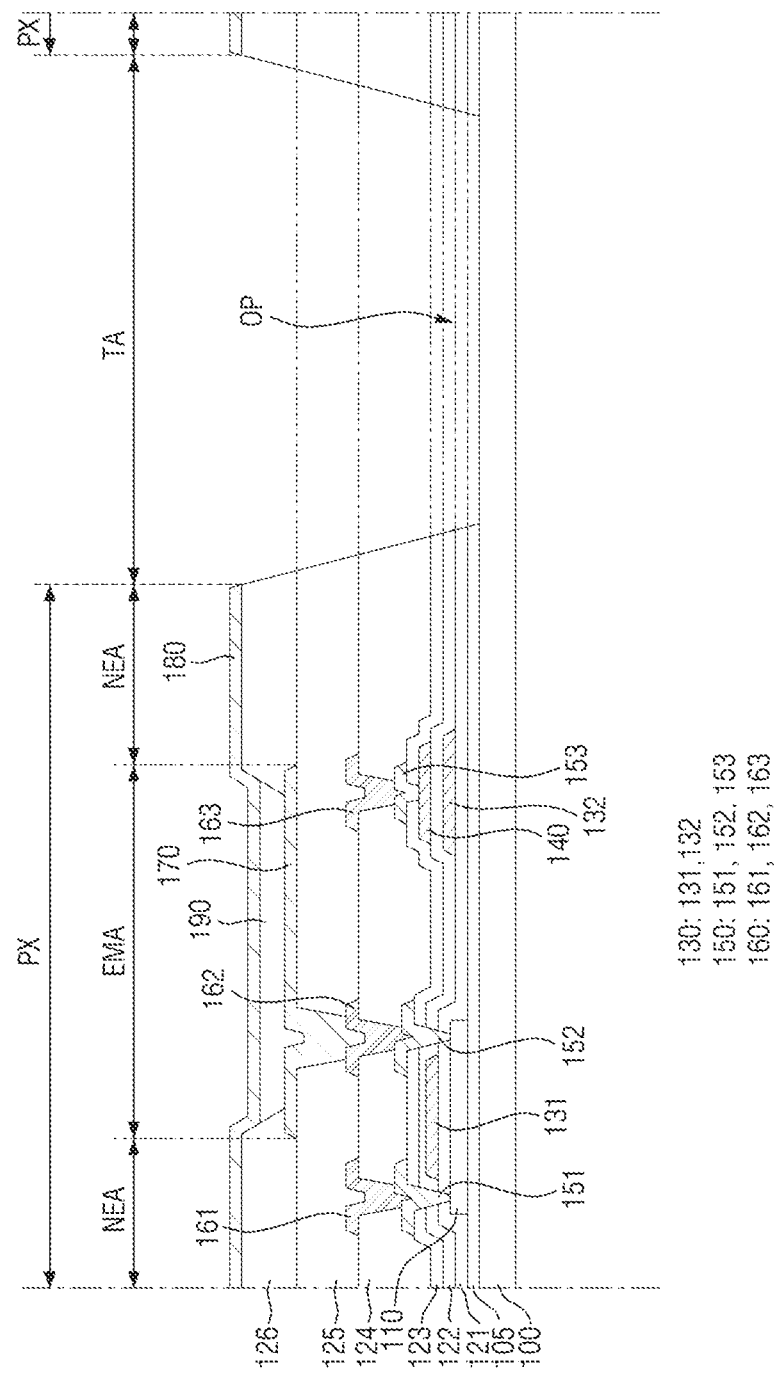
FIG. 40 is a cross-sectional view of a pixel and a light transmission part of a display panel according to another exemplary embodiment.

The sixth conductive layer 180 is disposed on the pixel definition film 126 and the organic layer 190. A cathode electrode, which is a common electrode, may be formed of the sixth conductive layer 180. The cathode electrode may be disposed not only in the emission area EMA of the pixel PX but also in the non-emission area NEA of the pixel PX (as illustrated in FIGS. 39-40). That is, the cathode electrode may be disposed on an entire surface of each pixel PX. The sixth conductive layer 180 may include a material layer having a low work function, which is made of one selected from Li, Ca, LiF/Ca, LiF/Al, Al, Mg, Ag, Pt, Pd, Ni, Au Nd, Ir, Cr, BaF, Ba, or a compound or mixture thereof (for example, a mixture of Ag and Mg). The sixth conductive layer 180 may further include a transparent metal oxide layer disposed on the material layer that has a low work function.

In one exemplary embodiment, an encapsulation film may be disposed on the sixth conductive layer 180. The encapsulation film may include an inorganic film. In one exemplary embodiment, the encapsulation film may include a first inorganic film, an organic film above the first inorganic film, and a second inorganic film above the organic film.

Hereinafter, a cross-sectional structure of a light transmission part TA will be described in more detail. The light transmission part TA has a structure in which some layers are removed in (or omitted from) a stacked structure of the pixel PX. Because the light transmission part TA is an area which does not emit light, layers that correspond to the anode electrode, the organic light-emitting layer, the cathode electrode, and/or the like may be omitted in one or more exemplary embodiments. Due to the omission of the layers, the light transmission part TA may have a transmittance higher than that of the pixel PX.

For example, the sixth conductive layer 180, which is a cathode electrode, is not disposed in the light transmission part TA. The cathode electrode is a common electrode, and the sixth conductive layer 180 is disposed in an entire region of the pixel PX. However, the sixth conductive layer 180 is removed in (or omitted from) the light transmission part TA to form a light transmission opening OP. The light transmission opening OP may be defined by the sixth conductive layer 180. In a top emission type panel, the cathode electrode transmits a certain amount of light but reflects or absorbs a significant amount of light. The sixth conductive layer 180, which is a cathode electrode, is not disposed in the light transmission part TA so that higher transmittance may be secured as compared with the non-emission area NEA of the pixel PX.

In addition, the fifth conductive layer 170, which is an anode electrode, may not be disposed in the light transmission part TA. In the top emission type panel, the anode electrode includes the reflective material layer as described above, and light may be transmitted in a thickness direction of the light transmission part TA because the fifth conductive layer 170 itself is not disposed in the light transmission part TA. In addition, because the organic layer 190 is not disposed in the light transmission part TA, higher transmittance may be maintained. Furthermore, the semiconductor layer or other conductive layers may not be disposed in the light transmission part TA.

Accordingly, as shown in FIG. 39, an exemplary stacked structure of the light transmission part TA may include the substrate 100, the buffer layer 105, the first insulating layer 121, the second insulating layer 122, the third insulating layer 123, the fourth insulating layer 124, the fifth insulating layer 125, and the pixel definition film 126.

FIG. 40 is a cross-sectional view of a pixel and a light transmission part of a display panel according to another exemplary embodiment. FIG. 40 illustrates that insulating films of a light transmission part TA may be omitted from the structure of FIG. 39.

That is, as shown by a solid line in FIG. 40, in the light transmission part TA, a pixel definition film 126, a fifth insulating layer 125, a fourth insulating layer 124, a third insulating layer 123, a second insulating layer 122, a first insulating layer 121, and a buffer layer 105 may be all removed (or omitted), and a surface of a substrate 100 may be exposed. A light transmission opening OP may be defined by a sixth conductive layer 180, the pixel definition film 126, the fifth insulating layer 125, the fourth insulating layer 124, the third insulating layer 123, the second insulating layer 122, the first insulating layer 121, and the buffer layer 105. The substrate 100 may still not be removed (or omitted) in the light transmission part TA. That is, the substrate 100 may overlap the light transmission part TA and may not have a through-hole in the light transmission part TA. As described above, in the case of the exemplary embodiment described with reference to FIG. 40, the transmittance of the light transmission part TA may be further improved as compared with the exemplary embodiment described with reference to FIG. 39 by further removing one or more insulating layers (e.g., multiple insulating layers in the case of the embodiment of FIG. 40 compared with the embodiment of FIG. 39).

As another example, as illustrated by a dotted line in FIG. 40, in the light transmission part TA, some portion among the pixel definition film 126, the fifth insulating layer 125, the fourth insulating layer 124, the third insulating layer 123, the second insulating layer 122, the first insulating layer 121, and the buffer layer 105 may be removed (or omitted). For example, the fourth insulating layer 124, which corresponds to a via layer, and all the layers positioned above the fourth insulating layer 124 may be removed (or omitted) to form the light transmission opening OP, but the present disclosure is not limited thereto.

According to a display device according to one exemplary embodiment, a blood pressure measuring module can be integrated into the display device without adding complex components.

Effects according to the exemplary embodiments of the present disclosure are not limited by the content exemplified above, and more various effects are included in the present specification.

In concluding the detailed description, those skilled in the art will appreciate that many variations and modifications can be made to the embodiments without substantially departing from the principles of the present invention. Therefore, the disclosed embodiments of the invention are used in a generic and descriptive sense only and not for purposes of limitation. While the present invention has been particularly shown and described with reference to some example embodiments thereof, it will be understood by those of ordinary skill in the art that various changes in form and details may be made therein without departing from the spirit and scope of the present invention as set forth in the following claims and their equivalents.

What is claimed is:

1. A display device comprising:
a display panel to display an image; and
a blood pressure measuring module comprising a pressure sensor, a pulse wave sensor and a controller,
wherein the pressure sensor is configured to sense a pressure that is applied to the display panel,
wherein the pulse wave sensor is configured to generate a pulse wave signal using light that is emitted from a pixel of the display panel,
wherein the pulse wave sensor comprises an optical sensor,
wherein the controller is configured to measure a blood pressure utilizing a pressure signal, which is sensed by the pressure sensor, and the pulse wave signal that is received from the pulse wave sensor, and
wherein the pressure sensor and the optical sensor overlap the display panel in a thickness direction of the display panel.

2. The display device of claim 1, wherein the pressure sensor and the optical sensor overlap each other in the thickness direction of the display panel.

3. The display device of claim 2, wherein the optical sensor is below the display panel, and wherein the pressure sensor is transparent and is between the display panel and the optical sensor.

4. The display device of claim 2, wherein the optical sensor is below the display panel, and wherein the pressure sensor is transparent and is above the display panel.

5. The display device of claim 1, wherein the display device includes a display area and a non-display area, and wherein the pressure sensor and the optical sensor are in the display area.

6. The display device of claim 1, wherein the blood pressure measuring module is configured to concurrently measure blood pressures at a plurality of points above the display panel.

7. The display device of claim 1, wherein the display panel comprises a plurality of pixel electrodes and a common electrode, the common electrode having a light transmission opening, and
wherein the optical sensor overlaps the light transmission opening.

8. The display device of claim 1, wherein the pressure sensor comprises a force sensor, a gap capacitor, or a strain gauge.

9. The display device of claim 1, further comprising a window member that is above the display panel.

10. The display device of claim 9, wherein the window member comprises a glass having a thickness of about 0.2 mm or less or a transparent polymer having a thickness of about 0.1 mm or less.

11. A display device comprising:
a display panel to display an image; and
a blood pressure measuring module comprising a pressure sensor, a pulse wave sensor and a controller,
wherein the pressure sensor is configured to sense a pressure that is applied to the display panel,
wherein the pulse wave sensor is configured to generate a pulse wave signal using light that is emitted from a pixel of the display panel,
wherein the pulse wave sensor comprises an optical sensor,
wherein the controller is configured to measure a blood pressure utilizing a pressure signal, which is sensed by the pressure sensor, and the pulse wave signal that is received from the pulse wave sensor, and
wherein the optical sensor is outside the display panel, and the pressure sensor overlaps the display panel in a thickness direction of the display panel.

12. The display device of claim 11, wherein the optical sensor overlaps the pressure sensor.

13. The display device of claim 11, wherein the optical sensor does not overlap the pressure sensor and is positioned within a distance of about 30 mm from the pressure sensor in a direction parallel to a display area of the display panel.

14. A display device comprising:
a display panel that comprises a display area including a first area and a second area;
a pressure sensor that overlaps the display panel in a thickness direction; and
an optical sensor that is below the display panel and overlaps the first area of the display panel,
wherein the first area of the display panel comprises a plurality of first pixels and a light transmission part,
wherein the second area of the display panel comprises a plurality of second pixels,
wherein the light transmission part has a light transmittance higher than that of the first pixels and the second pixels, and
wherein the first area of the display panel has a light transmittance higher than that of the second area of the display panel.

15. The display device of claim 14, wherein the pressure sensor overlaps the optical sensor in the thickness direction or is positioned within a distance of about 30 mm from the optical sensor in a direction parallel to the display area of the display panel.

16. The display device of claim 15, wherein the pressure sensor is transparent and is between the optical sensor and the display panel.

17. The display device of claim 15, wherein the optical sensor is to utilize light that is emitted from a pixel of the display panel in the display area.

18. The display device of claim 14, wherein the display panel comprises a plurality of pixel electrodes and a common electrode,
wherein each of the pixel electrodes is over the first area of the display panel and the second area of the display panel,
wherein the common electrode is on an entire surface in the second area of the display panel, and
wherein the common electrode is in a region of the first area of the display panel and defines a light transmission opening.

* * * * *